(12) United States Patent
Ignatyev et al.

(10) Patent No.: US 9,518,068 B2
(45) Date of Patent: Dec. 13, 2016

(54) COMPOUNDS CONTAINING HYDRIDO-TRICYANO-BORATE ANIONS

(75) Inventors: Nikolai (Mykola) Ignatyev, Duisburg (DE); Michael Schulte, Bischofsheim (DE); Kentaro Kawata, Kanagawa (JP); Tomohisa Goto, Sagamihara (JP); Eduard Bernhardt, Wuppertal (DE); Vera Bernhardt-Pitchougina, Wuppertal (DE); Helge Willner, Muehlheim/Ruhr (DE)

(73) Assignee: MERCK PATENT GMBH, Darmstadt (DE)

( * ) Notice: Subject to any disclaimer, the term of this patent is extended or adjusted under 35 U.S.C. 154(b) by 225 days.

(21) Appl. No.: 14/119,893

(22) PCT Filed: May 23, 2012

(86) PCT No.: PCT/EP2012/002179
§ 371 (c)(1),
(2), (4) Date: Nov. 25, 2013

(87) PCT Pub. No.: WO2012/163489
PCT Pub. Date: Dec. 6, 2012

(65) Prior Publication Data
US 2014/0107341 A1     Apr. 17, 2014

(30) Foreign Application Priority Data
May 31, 2011   (EP) .................................. 11004431

(51) Int. Cl.
*C07F 5/02*     (2006.01)
*H01L 51/50*    (2006.01)
*C07F 5/00*     (2006.01)
*H01M 10/0563*  (2010.01)

(52) U.S. Cl.
CPC .............. *C07F 5/025* (2013.01); *C07F 5/006* (2013.01); *C07F 5/022* (2013.01); *C07F 5/027* (2013.01); *H01M 10/0563* (2013.01)

(58) Field of Classification Search
USPC ..................... 548/110, 405; 546/13; 313/504
See application file for complete search history.

(56) References Cited

U.S. PATENT DOCUMENTS

| | | |
|---|---|---|
| 6,815,119 B2 | 11/2004 | Schmidt et al. |
| 7,713,658 B2 | 5/2010 | Mizuta et al. |
| 7,914,927 B2 | 3/2011 | Mizuta et al. |
| 8,124,869 B2 | 2/2012 | Mizuta et al. |
| 2002/0090547 A1 | 7/2002 | Schmidt et al. |
| 2004/0002002 A1 | 1/2004 | Mizuta et al. |
| 2004/0163700 A1 | 8/2004 | Mizuta et al. |
| 2010/0173195 A1 | 7/2010 | Mizuta et al. |

FOREIGN PATENT DOCUMENTS

| | | |
|---|---|---|
| CN | 1772728 A | 5/2006 |
| EP | 1205480 A2 | 5/2002 |
| JP | 2004-127774 A | 4/2004 |
| JP | 2008-159865 A | 7/2008 |

OTHER PUBLICATIONS

Chizmeshya, A.V.G. et al.: Synthesis of molecular adducts of beryllium, boron, and gallium cyanides: Theoretical and experimental correlations between solid-state and molecular analogues. Chem. Mater., vol. 19, pp. 5890-5901, 2007.*
International Search Report from PCT/EP2012/002179 dated Sep. 5, 2012.
E. Bernhardt et al. "Die Tetracyanoborate M[B(CN)4], M=[Bu4N]+, Ag+, K+" Z. Anorg. Allg. Chem., [2000], vol. 626, pp. 560-568.
E. Bernhardt et al. "An efficient synthesis of tetracyanoborates by sintering processes" Department of Inorganic Chemistry, University of Duisburg, [2003], vol. 629, 12 pages.
E. Bernhardt et al. "Synthesis and Properties of the Tetrkis(trifluoromethyl)borate Anion, [B(CF3)4]-: Structure Determination of Cs[B(CF3)4] by Single-Crystal X-ray Diffraction" Chem. Eur. J., [2001], vol. 7, No. 21, pp. 4696-4705.
Yanqiang Zhang et al. "Dicyanoborate-Based Ionic Liquids as Hypergolic Fluids" Angew. Chem., [2011], vol. 123, pp. 965-967.
Bela Gyori et al. "Preparation and Properties of Novel Cyano and Isocyano Derivatives of Borane and the Tetrahydroborate Anion" Journal of Organometallic Chemistry, [1983], vol. 255, pp. 17-28.
Haijun Yao et al. "Organo-Tricyanoborates as Tectons: Illustrative Coordination Polymers Based on Copper(I) Derivatives" Inorganic Chemistry, [2005], vol. 44, No. 18, pp. 6256-6264.
Bela Gyori et al. "Synthesis and characterization of cyanohydroisocyanoborates. Reactivity of the isocyano group towards nucleophiles" Polyhedron, vol. 17, No. 18, pp. 3175-3180, 1998.
E. Bernhardt et al. "Umpolung—at Boron by Reduction of [B(CN)4]- and Formation of the Dianion [B(CN)3]2-" Angew. Chem. Int. Ed., [2011], vol. 50, pp. 12085-12088.
English Abstract of JP 2008-159865—Publication Date: Jul. 10, 2008—Nippon Catalytic Chem Ind.
English Mechanical Translation of JP 2004-127774—Publication Date: Apr. 22, 2004—Nippon Catalytic Chem Ind.
Office Action for related Japanese Patent Application No. 2014-513074—Drafting Date:. Nov. 27, 2015—Dispatching Date: Dec. 4, 2015.

* cited by examiner

*Primary Examiner* — Charanjit Aulakh
(74) *Attorney, Agent, or Firm* — Millen White Zelano and Branigan, PC; Csaba Henter; Anthony Zelano

(57) ABSTRACT

The present invention relates to compounds containing hydrido-tricyano-borate anions, their preparation and their use, in particular as part of electrolyte formulations for electrochemical or optoelectronic devices.

14 Claims, No Drawings

COMPOUNDS CONTAINING HYDRIDO-TRICYANO-BORATE ANIONS

The present invention relates to compounds containing hydrido-tricyano-borate anions, their preparation and their use, in particular as part of electrolyte formulations for electrochemical or optoelectronic devices.

The salts according to the invention can on the one hand be used for the synthesis of ionic liquids, on the other hand the salts can be employed per se as ionic liquid.

Ionic liquids or liquid salts are ionic species which consist of an organic cation and a generally inorganic anion. They do not contain any neutral molecules and usually have melting points below 373 K.

The area of ionic liquids is currently the subject of intensive research since the potential applications are multifarious. Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten—neue Losungen für die Übergangsmetallkatalyse" [Ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227.

The properties of ionic liquids, for example melting point, thermal and electrochemical stability, viscosity, are strongly influenced by the nature of the anion.

E. Bernhardt et al, Z. Anorg. Allg. Chem. 2000, 626, 560, E. Bernhardt et al, Chem. Eur. J. 2001, 7, 4696 and E. Bernhardt et al, Z. Anorg. Allg. Chem. 2003, 629,1229 disclose the novel chemically and electrochemically stable borate anions $[B(CN)_4]^-$, $[F_xB(CN)_{4-x}]^-$, where x=1 to 3, and $[B(CF_3)_4]^-$.

EP 1205480 A1 describes tetrakisfluoroalkylborate salts and the use thereof as conductive salts or ionic liquids.

Compounds with dihydrido-dicyano-borate anions with organic cations such as N,N-dimethyl-N-butyl-hydrazinium, N,N-dimethyl-N-allyl-hydrazinium, 3-allyl-1-methylimidazolium, N-butylpyridinium, N-allylpyridinium, N-butyl-N-methyl-pyrrolidinium, N-allyl-N-methylpyrrolidinium, 1-butyl-3-methyltriazolium or 1-allyl-3-methyltriazolium cations are known from Zhang Y. and Shreeve J. M., Angew. Chem. 2011, vol. 123, p. 965-967. The above mentioned organic salts are synthesized via anion exchange-reaction with $Ag[BH_2(CN)_2]$.

But, silver salts are expensive materials. They are light sensitive, thermally not very stable and are not useful starting materials for industrial scale production of various salts, in particular the salts having organic cations and thus forming ionic liquids.

The object of the present invention was to provide alternative compounds which are novel, thermally and electrochemically stable which can be used for the synthesis of ionic liquids or as ionic liquids or as conductive salts, and which are in particular useful for the synthesis of ionic liquids or as ionic liquids or organic salts for application in electrochemical or optoelectronic devices. The object of the present invention was furthermore to provide a method for the preparation of the alternative salts, especially the compounds of formula I, as described below, which can be produced in economical way on industrial scale.

The object is achieved by the salts of the formula I according to the invention with hydrido-tricyano-borate anions and the described methods for their preparation.

The invention therefore relates to compounds of formula I

$$[Kt]^{z+}z[BH(CN)_3]^- \qquad \qquad I$$

in which $[Kt]^{z+}$ denotes an inorganic or organic cation and z is 1, 2, 3 or 4, where sodium hydrido-tricyano-borate, potassium hydrido-tricyano-borate, silver hydrido-tricyano-borate and $[(Phenyl)_3P—N=N—P(Phenyl)_3]$hydrido-tricyano-borate are excluded.

The term tricyano-hydridoborate is used within the description equally to tricyanomonohydridoborate, hydridotricyanoborate or monohydridotricyanoborate.

CN 1772728A describes a process for the preparation of N-phenylhydroxylamine derivatives through reduction of nitobenzenes in which the reducing agent is described as being sodium borohydride, potassium borohydride, sodium hydrido-tricyano-borate, potassium hydrido-tricyano-borate, sodium hydrogen selenide or selenium potassium hydride. The synthesis of the sodium hydrido-tricyano-borate or potassium hydrido-tricyano-borate is not mentioned within this citation.

B. Györi et al, Journal of Organometallic Chemistry, 255, 1983, 17-28 describes the isomerisation of sodium triisocyanohydroborate (adduct with 0.5 mol of dioxane) to sodium hydrido-tricyano-borate in boiling n-dibutyl ether and a preparation of silver hydrido-tricyano-borate through reaction of sodium hydrido-tricyanoborate with an aqueous solution of silver nitrate.

H. Yao et al, Inorg. Chem. 2005, 44, 6256-6264 describes the synthesis of silver triisocyanohydroborate $(Ag[HB(NC)_3])$ through reaction of $Me_2S*BHBr_2$ in $Me_2S$ with AgCN in $Me_2S$. The abbreviation Me means in this citation methyl. The crude material was reacted in a metathesis reaction with PPNCl forming $PPN[HB(NC)_3]$ which is then isomerised to $PPN[HB(CN)_3]$ in boiling n-butyl ether.

The cation $[Kt]^{z+}$ may be inorganic, in particular a metal cation, $H^+$ or $NO^+$. The metal cation may comprise metals from groups 1 to 12 of the Periodic Table. Preferred metal cations are metal cations, such as $Li^+$, $Na^+$, $K^+$, $Rb^+$, $Cs^+$, or $Mg^{2+}$, $Cu^+$, $Cu^{2+}$, $Zn^{2+}$, $Ca^{2+}$, $Y^{+3}$, $Yb^{+3}$, $La^{+3}$, $Sc^{+3}$, $Ce^{+3}$, $Nd^{+3}$, $Tb^{+3}$, $Sm^{+3}$ or complex (ligands containing) metal cations which include rare-earths, transitions or noble metals like rhodium, ruthenium, iridium, palladium, platinum, osmium, cobalt, nickel, iron, chromium, molybdenum, tungsten, vanadium, titanium, zirconium, hafnium, thorium, uranium, gold, where sodium hydrido-tricyano-borate, potassium hydrido-tricyano-borate or silver hydrido-tricyano-borate is excluded from the scope of the invented compounds but still included for the described methods for the preparations. The alkali metal is preferably lithium which is preferably used as conducting salt and/or component of electrolytes for application in batteries, capacitors, sensors or for electrochemical processes, and sodium or potassium which is preferably used for the synthesis of compounds of formula I as described above and below in which the cation $[Kt]^{z+}$ is a cation other than the used sodium or the used potassium, especially preferably for compounds of formula I in which the cation $[Kt]^{z+}$ is an organic cation.

If $[Kt]^{z+}$ is an organic cation, the organic cation is preferably selected from the group comprising iodonium, tritylium, sulfonium, oxonium, ammonium, phosphonium, uronium, thiouronium, guanidinium cations or heterocyclic cations.

Examples of organic cations are also polyammonium ions having a degree of charging of 4 which means z denotes 4.

Preferred compounds of formula I are compounds, in which $Kt^{z+}$ denotes an inorganic cation selected from the group of $H^+$, $NO^+$, $Li^+$, $Mg^{2+}$, $Cu^+$, $Cu^{2+}$, $Zn^{2+}$, $Ca^{2+}$, $Y^{+3}$, $Yb^{+3}$, $La^{+3}$, $Sc^{+3}$, $Ce^{+3}$, $Nd^{+3}$, $Tb^{+3}$, $Sm^{+3}$ or complex (ligands containing) metal cations which include rare-earths, transitions or noble metals like rhodium, ruthenium, iridium, palladium, platinum, osmium, cobalt, nickel, iron, chromium, molybdenum, tungsten, vanadium, titanium, zirconium, hafnium, thorium, uranium, gold, or an organic cation selected from the group of tritylium cation, in which the phenyl groups may be substituted by straight-chain or branched alkyl groups having 1 to 20 C atoms, straight-chain or branched alkenyl having 2 to 20 C atoms and one or more double bonds or straight-chain or branched alkynyl having 2 to 20 C atoms and one or more triple bonds, an oxonium cation of formula (1) or a sulfonium cation of formula (2)

$$[(R^o)_3O]^+ \quad (1)$$

$$[(R^o)_3S]^+ \quad (2),$$

where $R^o$ each independently of one another denotes a straight-chain or branched alkyl group having 1-8 C atoms, non-substituted phenyl or phenyl which is substituted by $R^{1*}$, OR', $N(R)_2$, CN or halogen and in case of sulfonium cations of formula (2) additionally denotes each independently $(R''')_2N$ and R' is independently of each other H, non-fluorinated, partially fluorinated or perfluorinated straight-chain or branched $C_1$- to $C_{18}$-alkyl, saturated $C_3$- to $C_7$-cycloalkyl, non-substituted or substituted phenyl, $R1^*$ is independently of each other non-fluorinated, partially fluorinated or perfluorinated straight-chain or branched $C_1$- to $C_{18}$-alkyl, saturated $C_3$- to $C_7$-cycloalkyl, non-substituted or substituted phenyl and R''' is independently of each other straight-chain or branched $C_1$ to $C_6$ alkyl;

an ammonium cation, which conforms to the formula (3)

$$[NR_4]^+ \quad (3),$$

where

R in each case, independently of one another, denotes H, OR', $N(R')_2$, with the proviso that a maximum of one R in formula (3) is OR' or $N(R')_2$, straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by straight-chain or branched alkyl groups having 1-6 C atoms, where one or two R may be fully substituted by halogens, in particular —F and/or —Cl, and one or more of the substituents R may be partially substituted by halogens, in particular —F and/or —Cl, and/or by —OH, —OR', —CN, —N(R')$_2$, —C(O)OH, —C(O)OR', —C(O)R', —C(O)N(R')$_2$, —SO$_2$N(R')$_2$, —C(O)X, —SO$_2$OH, —SO$_2$X, —NO$_2$, —SR', —S(O)R', —SO$_2$R' and where one or two non-adjacent carbon atoms in R which are not in the α-position may be replaced by atoms and/or atom groups selected from the group —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'— where R' each independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl and X each independently is halogen;

a phosphonium cation, which conforms to the formula (4)

$$[P(R^2)_4]^+ \quad (4),$$

where $R^2$ in each case, independently of one another, denotes H, OR' or $N(R')_2$, straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by straight-chain or branched alkyl groups having 1-6 C atoms, where one or two $R^2$ may be fully substituted by halogens, in particular —F and/or —Cl, and one or more of the substituents $R^2$ may be partially substituted by halogens, in particular —F and/or —Cl, and/or by —OH, —OR', —CN, —N(R')$_2$, —C(O)OH, —C(O)OR', —C(O)R', —C(O)N(R')$_2$, —SO$_2$N(R')$_2$, —C(O)X, —SO$_2$OH, —SO$_2$X, —NO$_2$, —SR', —S(O)R', —SO$_2$R' and where one or two non-adjacent carbon atoms in $R^2$ which are not in the α-position may be replaced by atoms and/or atom groups selected from the group —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'— where R' each independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl and X each independently is halogen;

a uronium cation, which conforms to the formula (5)

$$[C(NR^3R^4)(OR^5)(NR^6R^7)]^+ \quad (5),$$

where $R^3$ to $R^7$ each, independently of one another, denote H, where H is excluded for $R^5$, straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by straight-chain or branched alkyl groups having 1-6 C atoms, where one or two of the substituents $R^3$ to $R^7$ may be fully substituted by halogens, in particular —F and/or —Cl, and one or more of the substituents $R^3$ to $R^7$ may be partially substituted by halogens, in particular —F and/or —Cl, and/or by —OH, —OR', —N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', —NO$_2$ and where one or two non-adjacent carbon atoms in $R^3$ to $R^7$ which are not in the α-position may be replaced by atoms and/or atom groups selected from the group —O—, —S—, —S(O)—, —SO$_2$—, —SO$_2$O—, —C(O)—, —C(O)O—, —N$^+$(R')$_2$—, —P(O)R'O—, —C(O)NR'—,

—SO₂NR'—, —OP(O)R'O—, —P(O)(N(R')₂)NR'—, —P(R')₂=N— or —P(O)R'— where R' each independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl and X each independently is halogen;

a thiouronium cation, which conforms to the formula (6)

[C(NR³R⁴)(SR⁵)(NR⁶R⁷)]⁺    (6), where
R³ to R⁷ each, independently of one another, denote
H, where H is excluded for R⁵,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms,
where one or two of the substituents R³ to R⁷ may be fully substituted by halogens, in particular —F and/or —Cl, and one or more of the substituents R³ to R⁷ may be partially substituted by halogens, in particular —F and/or —Cl, and/or by —OH, —OR', —N(R')₂, —CN, —C(O)OH, —C(O)OR', —C(O)R', —C(O)N(R')₂, —SO₂N(R')₂, —C(O)X, —SO₂OH, —SO₂X, —SR', —S(O)R', —SO₂R', —NO₂ and where one or two non-adjacent carbon atoms in R³ to R⁷ which are not in the α-position may be replaced by atoms and/or atom groups selected from the group —O—, —S—, —S(O)—, —SO₂—, —SO₂O—, —C(O)—, —C(O)O—, —N⁺(R')₂—, —P(O)R'O—, —C(O)NR'—, —SO₂NR'—, —OP(O)R'O—, —P(O)(N(R')₂)NR'—, —P(R')₂=N— or —P(O)R'— where R' each independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl and X each independently is halogen;

a guanidinium cation, which conforms to the formula (7)

[C(NR⁸R⁹)(NR¹⁰R¹¹)(NR¹²R¹³)]⁺    (7), where
R⁸ to R¹³ each, independently of one another, denote
H, —CN, N(R')₂, —OR',
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms,
where one or two of the substituents R⁸ to R¹³ may be fully substituted by halogens, in particular —F and/or —Cl, and one or more of the substituents R⁸ to R¹³ may be partially substituted by halogens, in particular —F and/or —Cl, and/or by —OH, —OR', —N(R')₂, —CN, —C(O)OH, —C(O)OR', —C(O)R', —C(O)N(R')₂, —SO₂N(R')₂, —C(O)X, —SO₂OH, —SO₂X, —SR', —S(O)R', —SO₂R', —NO₂ and where one or two non-adjacent carbon atoms in R⁸ to R¹³ which are not in the α-position may be replaced by atoms and/or atom groups selected from the group —O—, —S—, —S(O)—, —SO₂—, —SO₂O—, —C(O)—, —C(O)O—, —N⁺(R')₂—, —P(O)R'O—, —C(O)NR'—, —SO₂NR'—, —OP(O)R'O—, —P(O)(N(R')₂)NR'—, —P(R')₂=N— or —P(O)R'—, where R' each independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl and X each independently is halogen;

a heterocyclic cation which conforms to the formula (8)

[HetN]^{z+}    (8)

where
HetN^{z+} denotes a heterocyclic cation selected from the group

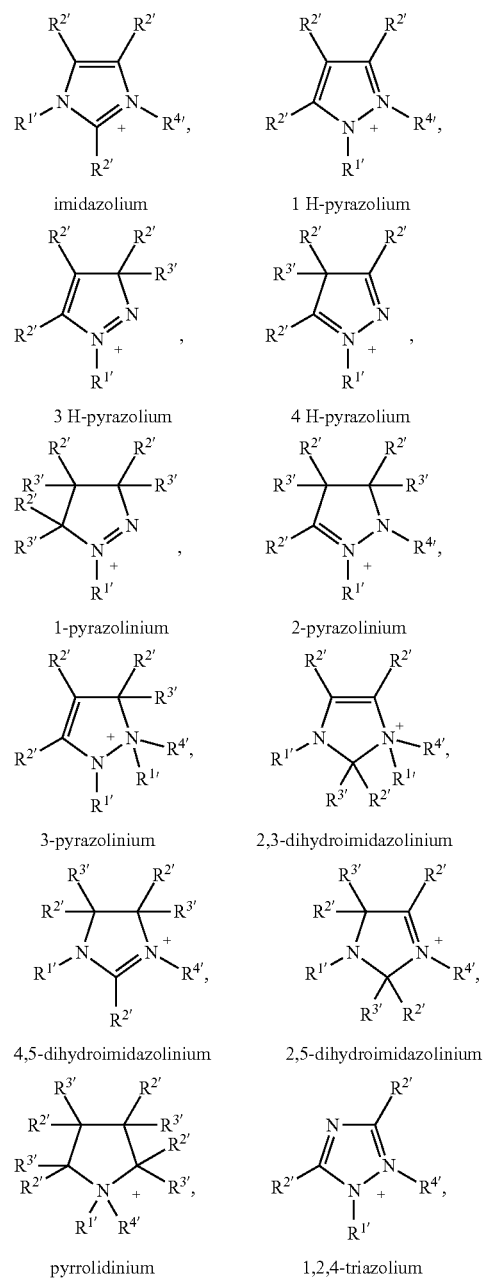

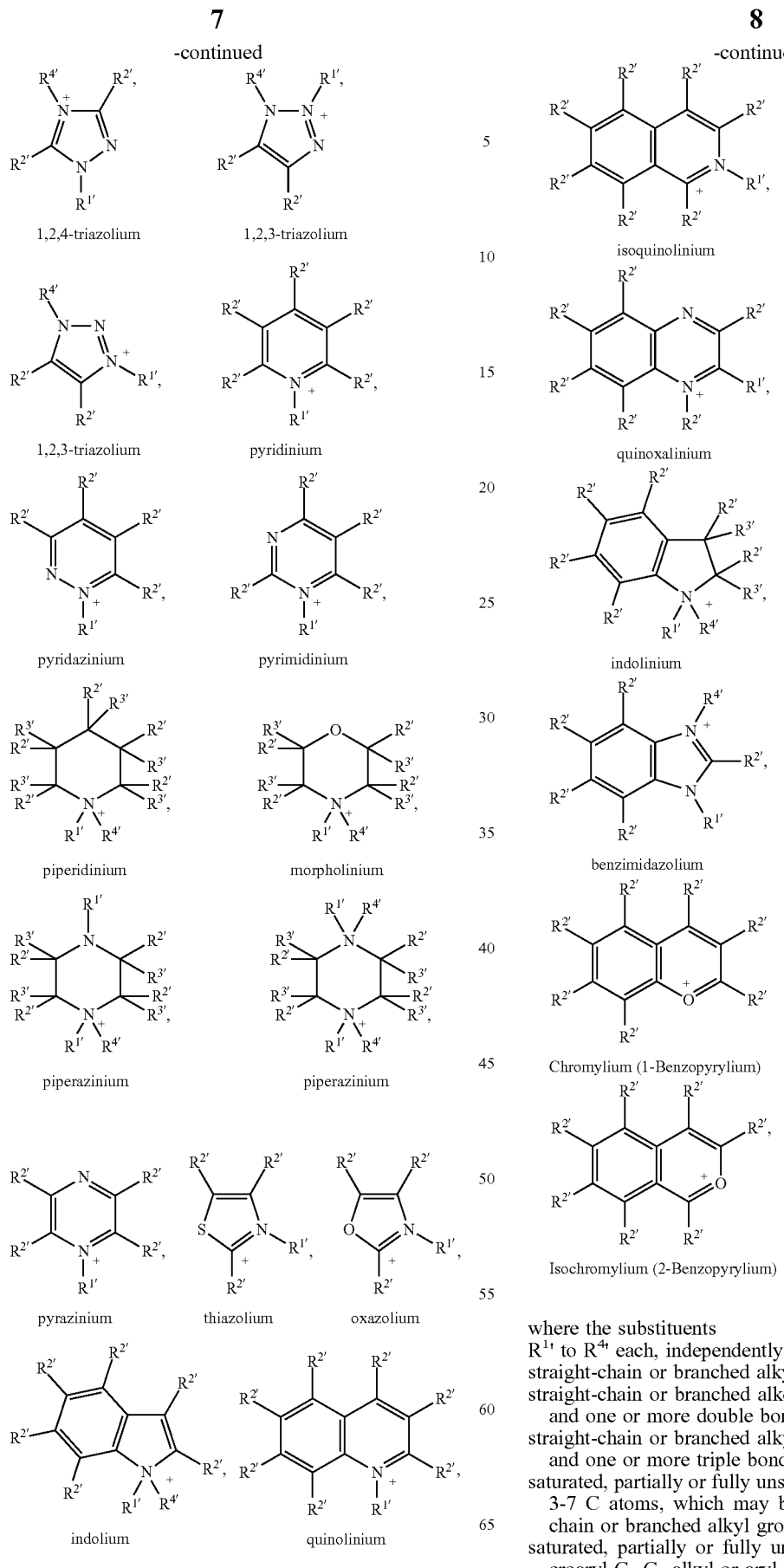

where the substituents
R¹' to R⁴' each, independently of one another, denote H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms,
saturated, partially or fully unsaturated heteroaryl, heteroaryl-$C_1$-$C_6$-alkyl or aryl-$C_1$-$C_6$-alkyl and $R^{2'}$ denote additionally F, Cl, Br, I, —CN, —OR', —N(R')$_2$, —P(O)(R')$_2$, —P(O)(OR')$_2$, —P(O)(N(R')$_2$)$_2$, —C(O)R', —C(O)OR', —C(O)X, —C(O)N(R')$_2$, —SO$_2$N(R')$_2$, —SO$_2$OH, —SO$_2$X, —SR', —S(O)R', —SO$_2$R' and/or NO$_2$, with the proviso that $R^{1'}$, $R^{3'}$, $R^{4'}$ are in this case independently of each other H and/or a straight-chain or branched alkyl having 1-20 C atoms, straight-chain or branched alkenyl having 2-20 C atoms and one or more double bonds, where the substituents $R^{1'}$, $R^{2'}$, $R^{3'}$ and/or $R^{4'}$ together may also form a ring system, where one to three substituents $R^{1'}$ to $R^{4'}$ may be fully substituted by halogens, in particular —F and/or —Cl, and one or more substituents $R^{1'}$ to $R^{4'}$ may be partially substituted by halogens, in particular —F and/or —Cl, and/or by —OH, —OR', N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', —NO$_2$, but where $R^{1'}$ and $R^{4'}$ cannot simultaneously be fully substituted by halogens and where, in the substituents $R^{1'}$ to $R^{4'}$, one or two non-adjacent carbon atoms which are not bonded to the heteroatom may be replaced by atoms and/or atom groups selected from the —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'—, where R' each independently is H, non-fluorinated, partially fluorinated or perfluorinated straight-chain or branched C$_1$- to C$_{18}$-alkyl, saturated C$_3$- to C$_7$-cycloalkyl, non-substituted or substituted phenyl and X each independently is halogen or a iodonium cation which conforms to the formula (9)

(9)

where the aryl group Ar denotes each independently of each other aryl with 6 to 30 C atoms which is non-substituted or substituted with at least a straight-chain or branched alkyl group having 1 to 20 C atoms, a straight-chain or branched alkenyl group having 2 to 20 C atoms and one or more double bonds, a straight-chain or branched alkynyl group having 2 to 20 C atoms and one or more triple bonds, $R^{1*}$, NO$_2$, SR', N(R')$_2$, CN and/or halogen and where R' each independently is H, non-fluorinated, partially fluorinated or perfluorinated straight-chain or branched C$_1$- to C$_{18}$-alkyl, saturated C$_3$- to C$_7$-cycloalkyl, non-substituted or substituted phenyl and where $R^{1*}$ each independently is non-fluorinated, partially fluorinated or perfluorinated straight-chain or branched C$_1$- to C$_{18}$-alkyl, saturated C$_3$- to C$_7$-cycloalkyl, non-substituted or substituted phenyl and halogen is F, Cl, Br or I.

Halogen is preferably F, Cl or Br, particularly preferably F or Cl.

The compounds of formula I having organic cations are possessing low viscosity. Some of the viscosities are even lower compared with the corresponding tetracyanoborates having the same organic cation. For example, 1-ethyl-3-methyl-imidazolium tetracyanoborate (emim TCB) has the dynamic viscosity of 22 mPas (at 20° C.) and the corresponding 1-ethyl-3-methyl-imidazolium hydrido-tricyanoborate has a viscosity of 12.2 mPas (at 20° C.). In addition, the thermal stability of such compounds is higher compared to compounds with organic cations with dihydrido-dicyanoborate anions or difluorodicyanoborate anions. For example, emim difluoro-dicyanoborate has a thermal stability up to 160° C., emim dihydrido-dicyano-borate shows a thermal stability up to 230° C. and emim hydrido-tricyanoborate has a thermal stability up to 277° C. which is comparable to the stability of emim TCB. The positive influence of the replacement of one cyano-group with hydrogen on the viscosity of compounds of formula I compared to the compounds with tetracyanoborate anions is unexpected. In comparison to electron-withdrawing groups like fluor, perfluoroalkyl or cyano groups which are able to effectively delocalise the negative charge of borate anions, hydrogen practically does not participate in the stabilization of borate-anion. The introduction of one hydrogen atom to Boron should increase the coordination ability of the tricyano-hydrido borate anion, causing increase in the viscosity of ionic liquids with this anion. But the experimental results are totally opposite from the theoretical point of view.

Not being bound by that theory, it seams that the introduction of one hydrogen atom to Boron breaks the symmetry of tetracyano-borate anion resulting in strong decreasing of ionic liquids viscosity.

Another advantage of compounds of formula I is that they can be prepared from commercially available starting materials via a simple reaction protocol.

$R^o$ of the)[(R$^o$)$_3$O]$^+$ cation (formula (1)) is preferably straight-chain alkyl having 1-8 C atoms, preferably having 1-4 C atoms, in particular methyl or ethyl, very particularly preferably ethyl.

$R^o$ of the)[(R$^o$)$_3$S]$^+$ cation (formula (2)) is preferably straight-chain alkyl having 1-8 C atoms, preferably having 1-4 C atoms, in particular methyl or ethyl, very particularly preferably ethyl. This definition is preferably for the technical application as component of an electrolyte.

At least one substitutent $R^0$ within the sulfonium cations of formula (2) is preferably phenyl or substituted phenyl in case the sulfonium cation is chosen together with the inventive anion as cationic polymerization initiator, photo-polymerization initiator or photo-acid generator. Particularly preferably all substituents $R^0$ in formula (2) are for this application each independently phenyl and/or phenyl substituted with SR' where R' has a meaning as described before.

Preferred cations of formula (2) for this application are triphenylsulfonium, diphenyltolylsulfonium, diphenylethylsulfonium, diphenyl-2,2,2-trifluorethyl sulfonium, diphenyl-2-ethoxy-ethylsulfonium, diphenyl-2-chlorethylsulfonium, diphenyl-3-brompropylsulfonium, diphenyl-3-chlorpropylsulfonium, diphenyl-3-cyanopropylsulfonium, diphenylallylsulfonium, diphenyl-4-pentenylsulfonium, diphenylpropargylsulfonium, diphenylbenzylsulfonium, diphenyl(p-cyanobenzyl)sulfonium, diphenyl(p-methylbenzyl)sulfonium, diphenyl(p-phenylthiobenzyl)sulfonium, diphenyl(3,3-dicyano-2-phenyl-2-propenyl)sulfonium, diphenyl(p-methylphenacyl)sulfonium, diphenyl(ethylcarboxy)methylsulfonium, diphenyl(n-octyl)sulfonium, diphenyl(n-octadecyl)sulfonium, diphenyl(w-carboxytridecyl)sulfonium, diphenyl(3-oxypropyl)sulfonium, diphenyl(w-carboxydodecyl)sulfonium, dihexyl-phenylsulfonium, ditolylphenylsulfonium, tritolylsulfonium, m- or p-(tert-butyl)phenyl-diphenylsulfonium, m- or p-methoxyphenyl-diphenylsulfonium, m- or p-CN-phenyl-diphenylsulfonium, m- or p-C$_6$H$_{13}$S-phenyl-diphenylsulfonium, m- or p-C$_6$H$_5$S-phenyl-diphenylsulfonium, Tri(p-methoxyphenyl)sulfonium, tri[4-(4-acetyl-phenylsulfanyl)phenyl]sulfonium, tri(4-tert.-butylphenyl)sulfonium.

For the purposes of the present invention, fully unsaturated cycloalkyl substituents are also taken to mean aromatic substituents.

In accordance with the invention, suitable substituents R and $R^2$ to $R^{13}$ of the compounds of the formulae (3) to (7) are preferably: H, $C_1$- to $C_{20}$-, in particular $C_1$- to $C_{14}$-alkyl groups, and saturated or unsaturated, i.e. also aromatic, $C_3$- to $C_7$-cycloalkyl groups, which may be substituted by $C_1$- to $C_6$-alkyl groups, in particular phenyl which may be substituted by $C_1$- to $C_6$-alkyl groups.

The substituents R and $R^2$ in the compounds of the formula (3) or (4) may be identical or different. The substituents R and $R^2$ are preferably different.

The substituents R and $R^2$ are particularly preferably methyl, ethyl, isopropyl, propyl, butyl, sec-butyl, pentyl, hexyl, octyl, decyl or tetradecyl.

Up to four substituents of the guanidinium cation $[C(NR^8R^9)(NR^{10}R^{11})(NR^{12}R^{13})]^+$ may also be bonded in pairs in such a way that mono-, bi- or polycyclic cations are formed.

Without restricting generality, examples of such guanidinium cations are:

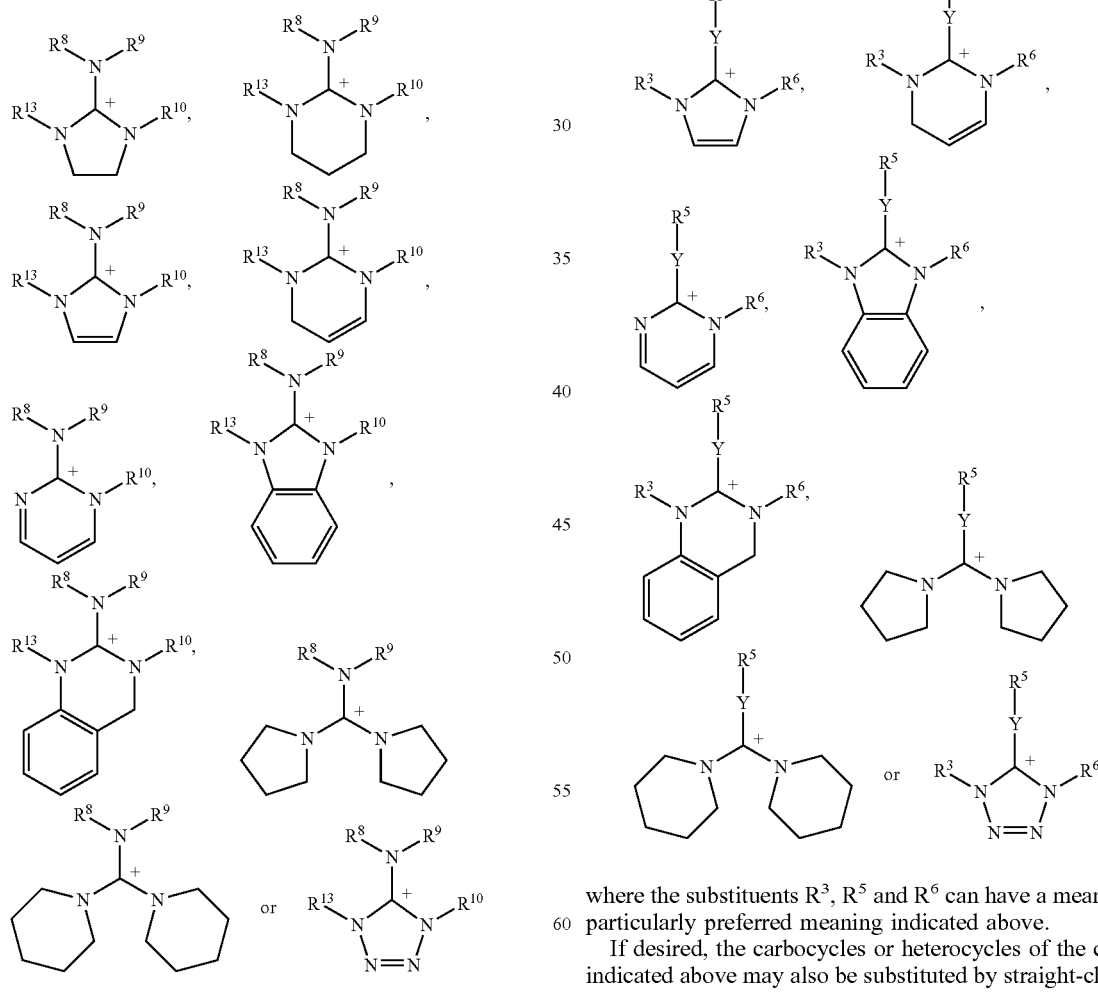

where the substituents $R^8$ to $R^{10}$ and $R^{13}$ can have a meaning or particularly preferred meaning indicated above.

If desired, the carbocycles or heterocycles of the guanidinium cations indicated above may also be substituted by straight-chain or branched $C_1$- to $C_6$-alkyl, straight-chain or branched $C_1$- to $C_6$-alkenyl, —CN, —NO$_2$, F, Cl, Br, I, OH, straight-chain or branched $C_1$-$C_6$-alkoxy, —N(R')$_2$, —SR', —S(O)R', —SO$_2$R', —COOH, —C(O)OR', —C(O)R', —C(O)N(R')$_2$, —SO$_2$N(R')$_2$, —C(O)X, —SO$_2$X, —SO$_3$H, substituted or non-substituted phenyl or a non-substituted or substituted heterocycle, where X and R' have a meaning indicated above.

Up to four substituents of the uronium cation $[C(NR^3R^4)(OR^5)(NR^6R^7)]^+$ or thiouronium cation $[C(NR^3R^4)(SR^5)(NR^6R^7)]^+$ may also be bonded in pairs in such a way that mono-, bi- or polycyclic cations are formed.

Without restricting generality, examples of such cations are indicated below, where Y=O or S:

where the substituents $R^3$, $R^5$ and $R^6$ can have a meaning or particularly preferred meaning indicated above.

If desired, the carbocycles or heterocycles of the cations indicated above may also be substituted by straight-chain or branched $C_1$- to $C_6$-alkyl, straight-chain or branched $C_1$- to $C_6$-alkenyl, —CN, —NO$_2$, F, Cl, Br, I, OH, straight-chain or branched $C_1$-$C_6$-alkoxy, —N(R')$_2$, —SR', —S(O)R', —SO$_2$R', —COOH, —C(O)OR', —C(O)R', —C(O)N(R')$_2$, —SO$_2$N(R')$_2$, —C(O)X, —SO$_2$X, —SO$_3$H, substituted or non-substituted phenyl or a non-substituted or substituted heterocycle, where X and R' have a meaning indicated above.

The substituents $R^3$ to $R^{13}$ are each, independently of one another, preferably a straight-chain or branched alkyl group having 1 to 16 C atoms. The substituents $R^3$ and $R^4$, $R^6$ and $R^7$, $R^8$ and $R^9$, $R^{10}$ and $R^{11}$ and $R^{12}$ and $R^{13}$ in compounds of the formula (5) to (7) may be identical or different. $R^3$ to $R^{13}$ are particularly preferably each, independently of one another, methyl, ethyl, n-propyl, iso-propyl, n-butyl, tert-butyl, sec-butyl, phenyl, hexyl or cyclohexyl, very particularly preferably methyl, ethyl, n-propyl, iso-propyl, n-butyl or hexyl.

In accordance with the invention, suitable substituents $R^{1'}$ to $R^{4'}$ of compounds of the formula (8) are each, independently of one another, preferably,

H, straight-chain or branched alkyl having 1 to 20 C atoms, which optionally may be fluorinated or perfluorinated, straight-chain or branched alkenyl having 2 to 20 C atoms and one or more double bonds, which optionally may be fluorinated, straight-chain or branched alkynyl having 2 to 20 C atoms and one or more triple bonds which optionally may be fluorinated or straight-chain or branched alkoxyalkyl having 2 to 8 C atoms, with the assumption that $R^{1'}$ and $R^{4'}$ are not simultaneously be perfluorinated.

The substituents $R^{1'}$ and $R^{4'}$ are each, independently of one another, particularly preferably straight-chain or branched alkyl having 1 to 20 C atoms, which optionally may be fluorinated or perfluorinated or straight-chain or branched alkoxyalkyl having 2 to 8 C atoms with the assumption that $R^{1'}$ and $R^{4'}$ are not perfluorinated at the same time.

The substituents $R^{1'}$ and $R^{4'}$ are each, independently of one another, particularly preferably methyl, ethyl, allyl, iso-propyl, propyl, butyl, sec-butyl, tert-butyl, n-pentyl, n-hexyl, n-octyl, n-decyl, cyclohexyl, methoxyethyl, methoxymethyl, ethoxyethyl, ethoxymethyl, phenyl or benzyl. They are very particularly preferably methyl, ethyl, propyl n-butyl or methoxyethyl. In pyrrolidinium, piperidinium or indolinium compounds, the two substituents $R^{1'}$ and $R^{4'}$ are preferably different.

In accordance with the invention, suitable substituents $R^{2'}$ and $R^{3'}$ of compounds of formula (8) are particularly preferably: H, straight-chain or branched $C_1$- to $C_{20}$-, in particular $C_1$- to $C_{12}$-alkyl groups, and saturated or unsaturated, i.e. also aromatic, $C_3$- to $C_7$-cycloalkyl groups, which may be substituted by straight-chain or branched $C_1$- to $C_6$-alkyl groups, in particular phenyl.

The substituent $R^{2'}$ or $R^{3'}$ is in each case, independently of one another, in particular H, methyl, ethyl, iso-propyl, propyl, butyl, sec-butyl, tert-butyl, cyclohexyl, phenyl or benzyl. $R^{2'}$ is particularly preferably H, methyl, ethyl, iso-propyl, propyl, butyl or sec-butyl. $R^{3'}$ is particularly preferably H. $R^{2'}$ and $R^{3'}$ are very particularly preferably H.

A straight-chain or branched alkyl having 1-20 C atoms denotes an alkyl group having 1, 2, 3, 4, 5, 6, 7, 8, 9, 10, 11, 12, 13, 14, 15, 16, 17, 18, 19 or 20 C atoms, for example methyl, ethyl, iso-propyl, n-propyl, iso-butyl, n-butyl, tert-butyl, n-pentyl, 1-, 2- or 3-methylbutyl, 1,1-, 1,2- or 2,2-dimethylpropyl, 1-ethylpropyl, n-hexyl, n-heptyl, n-octyl, ethylhexyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or eicosyl, which optionally may be fluorinated or perfluorinated. The term "perfluorinated" means that all H atoms are substituted by F atoms in the given alkyl group. The term "fluorinated" means that at least one H atom of the given alkyl group is substituted by an F atom.

A straight-chain or branched alkenyl having 2 to 20 C atoms, in which a plurality of double bonds may also be present, is, for example, allyl, 2- or 3-butenyl, iso-butenyl, sec-butenyl, furthermore 4-pentenyl, iso-pentenyl, hexenyl, heptenyl, octenyl, $-C_9H_{17}$, $-C_{10}H_{19}$ to $-C_{20}H_{39}$, preferably allyl, 2- or 3-butenyl, iso-butenyl, sec-butenyl, furthermore preferably 4-pentenyl, isopentenyl or hexenyl, which may be optionally partially fluorinated.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, heptynyl, octynyl, $-C_9H_{15}$, $-C_{10}H_{17}$ to $-C_{20}H_{37}$, preferably ethynyl, 1- or 2-propynyl, 2- or 3-butynyl, 4-pentynyl, 3-pentynyl or hexynyl, which may be optionally partially fluorinated.

A straight-chain or branched alkoxyalkyl having 2 to 12 C atoms is, for example, methoxymethyl, 1-methoxyethyl, 1-methoxypropyl, 1-methoxy-2-methyl-ethyl, 2-methoxypropyl, 2-methoxy-2-methyl-propyl, 1-methoxybutyl, 1-methoxy-2,2-dimethyl-ethyl, 1-methoxy-pentyl, 1-methoxyhexyl, 1-methoxy-heptyl, ethoxymethyl, 1-ethoxyethyl, 1-ethoxypropyl, 1-ethoxy-2-methyl-ethyl, 1-ethoxybutyl, 1-ethoxy-2,2-dimethyl-ethyl, 1-ethoxypentyl, 1-ethoxyhexyl, 1-ethoxyheptyl, propoxymethyl, 1-propoxyethyl, 1-propoxypropyl, 1-propoxy-2-methyl-ethyl, 1-propoxybutyl, 1-propoxy-2,2-dimethyl-ethyl, 1-propoxypentyl, butoxymethyl, 1-butoxyethyl, 1-butoxy-propyl or 1-butoxybutyl. Particularly preferred is methoxymethyl, 1-methoxyethyl, 2-methoxy-propyl, 1-methoxypropyl, 2-methoxy-2-methyl-propyl or 1-methoxybutyl.

Aryl with 6 to 30 C atoms denotes an aryl group with 6 to 30 C atoms and is an aromatic group with aromatic delocalized electrons, optionally substituted one or more times by $R^{1*}$, OR', $N(R')_2$, CN, $NO_2$ or halogen. An aryl group with 6 to 30 C atoms, preferably with 6 to 24 C atoms, is for example 1-, 2-, 3-, 4-, 5- or 6-phenyl, 1-, 2-, 3-, 4-, 6-, 7- or 8-naphthyl, 1-, 2-, 3-, 4-, 6-, 7- or 8-phenanthrenyl, 1-, 2-, 3-, 4-, 5-, 6-, 7-, 8-, 9- or 10-anthracenyl, 1-, 2-, 3-, 4-, 5-, 6-, 7-, 8-, 9-, 10-, 11- or 12-tetracenyl, 1-, 2-, 3-, 4-, 5-, 6-, 7-, 8-, 9-, 10-, 11- or 12-benzo[a]anthracenyl, 1-, 2-, 3-, 4-, 5-, 6-, 7-, 8-, 9-, 10-, 11-, 12-, 13- or 15-pentacenyl, 1-, 2-, 3-, 4-, 5-, 6-, 7-, 8-, 9-, 10-, 11- or 12-chrysenyl, 1-, 2-, 3-, 4-, 5-, 6-, 7-, 8-, 9- or 10-pyrenyl, 1-, 2-, 3-, 4-, 5-, 6-, 7-, 8-, 9-, 10-, 11- or 12-benzo[a]pyrenyl, 1-, 2-, 3-, 4-, 5-, 6-, 7- or 8-azulenyl, 1-, 2-, 3-, 4-, 5-, 6-, 7-, 8-, 9- or 10-fluoranthenyl, 1-, 2-, 3-, 4-, 5-, 6-, 7-, 8-, 9-, 10-, 11- or 12-perylenyl, 1-, 2-, 3-, 4-, 5-, 6- or 7-indenyl or 1-, 2-, 3-, 4-, 5-, 6-, 7-, 8- or 9-fluorenyl which is preferably non-substituted or substituted by $R^{1*}$, OR, $N(R)_2$, CN or halogen. Preferably, aryl denotes 1-, 2-, 3-, 4-, 5- or 6-phenyl, 1-, 2-, 3-, 4-, 6-, 7- or 8-naphthyl which is non-substituted or substituted by $R^{1*}$, OR', $N(R')_2$, CN or halogen. $R^{1*}$ and R' have a meaning as described above.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted, as described above, by halogens, in particular —F and/or —Cl, or partially by —OH, —OR', —N(R')$_2$, —CN, —C(O)OH, —C(O)N(R')$_2$, —SO$_2$N(R')$_2$, —C(O)X, —C(O)OR', —C(O)R', —SO₂OH, —SO₂X, —SR', —S(O)R', —SO₂R', —NO₂ and R' and X have a meaning as described above.

Non-substituted saturated or partially or fully unsaturated cycloalkyl groups having 3-7 C atoms are therefore cyclopropyl, cyclobutyl, cyclopentyl, cyclo-hexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by straight-chain or branched $C_1$- to $C_6$-alkyl groups, where the cycloalkyl group or the cycloalkyl group substituted by straight-chain or branched $C_1$- to $C_6$-alkyl groups may in turn also be substituted by halogen atoms, such as F, Cl, Br or I, in particular F or Cl, or by —OH, —OR', —N(R')₂, —CN, —C(O)OH, —C(O)N(R')₂, —SO₂N(R')₂, —C(O)X, —C(O)OR', —C(O)R', —SO₂OH, —SO₂X, —SR', —S(O)R', —SO₂R', —NO₂ and R' and X have a meaning as described above.

In the substituents R, $R^2$ to $R^{13}$ or $R^{1'}$ to $R^{4'}$, one or two non-adjacent carbon atoms which are not bonded in the α-position to the heteroatom may also be replaced by atoms and/or atom groups selected from the group O, —S—, —S(O)—, —SO₂—, —SO₂O—, —C(O)—, —C(O)O—, —N⁺R'₂—, —P(O)R'O—, —C(O)NR'—, —SO₂NR'—, —OP(O)R'O—, —P(O)(NR'₂)NR'—, —PR'₂=N— or —P(O)R'—, where R'
is non-fluorinated, partially fluorinated or perfluorinated $C_1$- to $C_{18}$-alkyl, saturated $C_3$- to $C_7$-cycloalkyl, non-substituted or substituted phenyl.

Without restricting generality, examples of substituents R, $R^2$ to $R^{13}$ and $R^{1'}$ to $R^{4'}$ modified in this way are:
—OCH₃, —OCH(CH₃)₂, —CH₂OCH₃, —CH₂—CH₂—O—CH₃, —C₂H₄OCH(CH₃)₂, —C₂H₄C₂H₅, —C₂H₄SCH(CH₃)₂, —S(O)CH₃, —SO₂CH₃, —SO₂C₆H₅, —SO₂C₃H₇, —SO₂CH(CH₃)₂, —SO₂CH₂CF₃, —CH₂SO₂CH₃, —O—C₄H₈—O—C₄H₉, —CF₃, —C₂F₅, —C₃F₇, —C₄F₉, —C(CF₃)₃, —CF₂SO₂CF₃, —C₂F₄N(C₂F₅)C₂F₅, —CHF₂, —CH₂CF₃, —C₂F₂H₃, —C₃H₆, —CH₂C₃F₇, —C(CFH₂)₃, —CH₂C(O)OH, —CH₂C₆H₅, —C(O)C₆H₅ or P(O)(C₂H₅)₂.

In R' or $R^{1*}$, $C_3$- to $C_7$-cycloalkyl is, for example, cyclopropyl, cyclobutyl, cyclo-pentyl, cyclohexyl or cycloheptyl.

In R' or $R^{1*}$, substituted phenyl denotes phenyl which is substituted by straight-chain or branched $C_1$- to $C_6$-alkyl, straight-chain or branched $C_1$- to $C_6$-alkenyl, —CN, —NO₂, F, Cl, Br, I, —OH, straight-chain or branched-$C_1$-$C_6$-alkoxy, N(R")₂, —COOH, —C(O)OR", —C(O)R", —SO₂X', —SR", —S(O)R", —SO₂R", SO₂N(R")₂ or SO₃H, where X' denotes F, Cl or Br and R" denotes a non-fluorinated, partially fluorinated or perfluorinated straight-chain or branched $C_1$- to $C_6$-alkyl or $C_3$- to $C_7$-cycloalkyl as defined for R', for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-nitrophenyl, o-, m- or p-hydroxyphenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, further preferably 2,3-, 2,4-, 2,5-, 2,6-, 3,4- or 3,5-dimethyl-phenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-di-methoxyphenyl, 5-fluoro-2-methylphenyl, 3,4,5-trimethoxyphenyl or 2,4,5-trimethylphenyl.

In $R^{1'}$ to $R^{4'}$, heteroaryl is taken to mean a saturated or unsaturated mono- or bicyclic heterocyclic group having 5 to 13 ring members, in which 1, 2 or 3 N and/or 1 or 2 S or O atoms may be present and the heterocyclic radical may be mono- or poly-substituted by straight-chain or branched $C_1$- to $C_6$-alkyl, straight-chain or branched $C_1$- to $C_6$-alkenyl, —CN, —NO₂, F, Cl, Br, I, —OH, —N(R")₂, straight-chain or branched $C_1$-$C_6$-alkoxy, —COOH, —C(O)OR", —C(O)R", —SO₂X', —SO₂N(R")₂, —SR", —S(O)R", —SO₂R" or SO₃H, where X' and R" have a meaning indicated above.

The heterocyclic group is preferably substituted or non-substituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Heteroaryl-$C_1$-$C_6$-alkyl is, analogously to aryl-$C_1$-$C_6$-alkyl, taken to mean, for example, pyridinylmethyl, pyridinylethyl, pyridinylpropyl, pyridinylbutyl, pyri-dinylpentyl, pyridinylhexyl, where the heterocycles described above may furthermore be linked to the alkylene chain in this way.

HetN$^{z+}$ is preferably

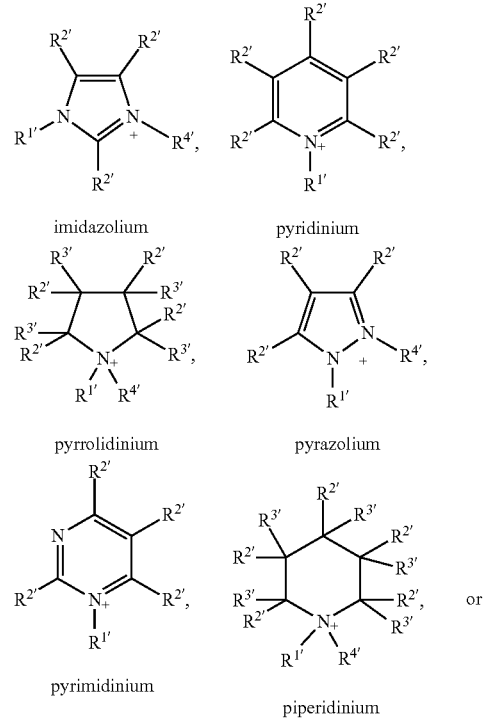

imidazolium          pyridinium pyrrolidinium        pyrazolium pyrimidinium         piperidinium -continued

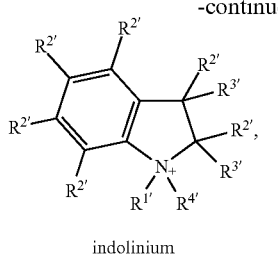
indolinium where the substituents $R^{1'}$ to $R^{4'}$ each, independently of one another, have a meaning described above.

$HetN^{z+}$ is particularly preferably

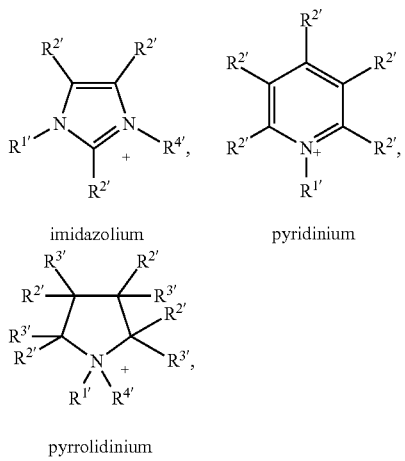
imidazolium        pyridinium pyrrolidinium where the substituents $R^{1'}$ to $R^{4'}$ each, independently of one another, have a meaning described above.

$HetN^{z+}$ is very particularly preferably

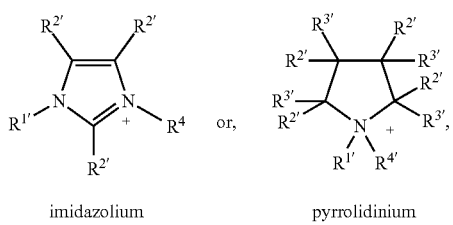
imidazolium        pyrrolidinium where the substituents $R^{1'}$ to $R^{4'}$ each, independently of one another, have a meaning described above. Preferred meanings of $R^{1'}$ to $R^{4'}$ within imidazolium or pyrrolidinium cations are defined in the following terms:

Preferred 1,1-dialkylpyrrolidinium cations are, for example, 1,1-dimethyl-pyrrolidinium, 1-methyl-1-ethylpyrrolidinium, 1-methyl-1-propylpyrrolidinium, 1-methyl-1-butylpyrrolidinium, 1-methyl-1-pentylpyrrolidinium, 1-methyl-1-hexylpyrrolidinium, 1-methyl-1-heptylpyrrolidinium, 1-methyl-1-octylpyrrolidinium, 1-methyl-1-nonylpyrrolidinium, 1-methyl-1-decylpyrrolidinium, 1,1-diethylpyrrolidinium, 1-ethyl-1-propylpyrrolidinium, 1-ethyl-1-butylpyrrolidinium, 1-ethyl-1-pentylpyrrolidinium, 1-ethyl-1-hexylpyrrolidinium, 1-ethyl-1-heptylpyrrolidinium, 1-ethyl-1-octylpyrrolidinium, 1-ethyl-1-nonylpyrrolidinium, 1-ethyl-1-decylpyrrolidinium, 1,1-dipropylpyrrolidinium, 1-propyl-1-methyl-pyrrolidinium, 1-propyl-1-butylpyrrolidinium, 1-propyl-1-pentylpyrrolidinium, 1-propyl-1-hexylpyrrolidinium, 1-propyl-1-heptylpyrrolidinium, 1-propyl-1-octylpyrrolidinium, 1-propyl-1-nonylpyrrolidinium, 1-propyl-1-decyl-pyrrolidinium, 1,1-dibutylpyrrolidinium, 1-butyl-1-methylpyrrolidinium, 1-butyl-1-pentylpyrrolidinium, 1-butyl-1-hexylpyrrolidinium, 1-butyl-1-heptyl-pyrrolidinium, 1-butyl-1-octylpyrrolidinium, 1-butyl-1-nonylpyrrolidinium, 1-butyl-1-decylpyrrolidinium, 1,1-dipentylpyrrolidinium, 1-pentyl-1-hexyl-pyrrolidinium, 1-pentyl-1-heptylpyrrolidinium, 1-pentyl-1-octylpyrrolidinium, 1-pentyl-1-nonylpyrrolidinium, 1-pentyl-1-decylpyrrolidinium, 1,1-dihexyl-pyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-dihexyl-pyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-diheptylpyrrolidinium, 1-heptyl-1-octylpyrrolidinium, 1-heptyl-1-nonylpyrrolidinium, 1-heptyl-1-decylpyrrolidinium, 1,1-dioctylpyrrolidinium, 1-octyl-1-nonyl-pyrrolidinium, 1-octyl-1-decylpyrrolidinium, 1,1-dinonylpyrrolidinium, 1-nonyl-1-decylpyrrolidinium or 1,1-didecylpyrrolidinium. Very particular preference is given to 1-butyl-1-methylpyrrolidinium or 1-propyl-1-methylpyrrolidinium.

Preferred 1-alkyl-1-alkoxyalkylpyrrolidinium cations are, for example, 1-methoxymethyl-1-methyl-pyrrolidinium, 1-methoxymethyl-1-ethyl-pyrrolidinium, 1-(2-methoxyethyl)-1-methylpyrrolidinium, 1-(2-methoxyethyl)-1-ethyl-pyrrolidinium, 1-(2-methoxyethyl)-1-propylpyrrolidinium, 1-(2-methoxyethyl)-1-butylpyrrolidinium, 1-(2-ethoxyethyl)-1-methylpyrrolidinium, 1-ethoxymethyl-1-methyl-pyrrolidinium, 1-ethoxymethyl-1-ethyl-pyrrolidinium. Very particular preference is given to 1-(2-methoxyethyl)-1-methylpyrrolidinium.

Preferred 1,3-dialkylimidazolium cations are, for example, 1-ethyl-3-methyl-imidazolium, 1-methyl-3-propylimidazolium, 1,2,3-trimethylimidazolium, 1-ethyl-2,3-dimethylimidazolium, 1-propyl-2,3-dimethylimidazolium, 1-butyl-2,3-dimethylimidazolium, 1-butyl-3-methylimidazolium, 1-methyl-3-pentylimidazolium, 1-ethyl-3-propylimidazolium, 1-butyl-3-ethylimidazolium, 1-ethyl-3-pentylimidazolium, 1-butyl-3-propylimidazolium, 1,3-dimethyl-imidazolium, 1,3-diethylimidazolium, 1,3-dipropylimidazolium, 1,3-dibutylimidazolium, 1,3-dipentylimidazolium, 1,3-dihexylimidazolium, 1,3-diheptylimidazolium, 1,3-dioctylimidazolium, 1,3-dinonylimidazolium, 1,3-didecylimidazolium, 1-hexyl-3-methylimidazolium, 1-heptyl-3-methylimidazolium, 1-methyl-3-octylimidazolium, 1-methyl-3-nonylimidazolium, 1-decyl-3-methylimidazolium, 1-ethyl-3-hexylimidazolium, 1-ethyl-3-heptylimidazolium, 1-ethyl-3-octylimidazolium, 1-ethyl-3-nonylimidazolium or 1-decyl-3-ethylimidazolium. Particularly preferred cations are 1-ethyl-3-methylimidazolium, 1-butyl-3-methylimidazolium or 1-methyl-3-propylimidazolium.

Preferred 1-alkoxyalkyl-3-alkylimidazolium cations are, for example 1-methoxymethyl-3-methylimidazolium, 1-methoxymethyl-3-ethylimidazolium, 1-methoxymethyl-3-butylimidazolium, 1-(2-methoxyethyl)-3-methylimidazolium, 1-(2-methoxyethyl)-3-ethylimidazolium, 1-(2-methoxyethyl)-3-propyl-imidazolium, 1-(2-methoxyethyl)-3-butylimidazolium, 1-(2-ethoxyethyl)-3-methylimidazolium, 1-ethoxymethyl-3-methylimidazolium.

Preferred 1-alkenyl-3-alkylimidazolium cations are, for example 1-allyl-3-methyl-imidazolium or 1-allyl-2,3-dimethylimidazolium.

Preferred cations of formula (9) are diphenyliodonium, ditolyliodonium, phenyltolyliodonium, tolyl-(4-sec.-butyl-phenyl)iodonium, di(p-tert-butylphenyl)iodonium, p-methoxyphenyl-phenyliodonium, di(p-methoxyphenyl)iodonium, m- or p-CN-phenyl-phenyliodonium, m- or p-(C$_6$H$_5$S)-phenyl-phenyliodonium.

The organic cations of the compounds of formula I according to the invention are preferably sulfonium, ammonium, phosphonium cations of formula (2), (3) and (4) or heterocyclic cations of formula (8), particularly preferably sulfonium cations of formula (2) or heterocyclic cations of formula (8) as described above, especially for the application as electrolyte component.

The organic cations of the compounds of formula I according to the invention are very particularly preferably heterocyclic cations of formula (8) in which HetN$^{z+}$ is as defined above, where the substituents R$^{1'}$ to R$^{4'}$ each, independently of one another, have a meaning described above for the application as electrolyte component. The organic cation of the compound of formula I is very particularly preferably imidazolium, where the substituents R$^{1'}$ to R$^{4'}$ each, independently of one another, have a meaning described above or has one of the particularly preferred meanings of 1,3-dialkylimidazolium, 1-alkenyl-3-alkylimidazolium or 1-alkoxyalkyl-3-alkylimidazolium as described above.

Particularly suitable organic cations of the formula I are for this application 1-butyl-1-methylpyrrolidinium, 1-ethyl-3-methylimidazolium, 1-ethyl-2,3-dimethylimidazolium, 1-(2-methoxyethyl)-3-methylimidazolium, 1-butyl-3-methylimidazolium, tributyl-methylammonium, tetra-n-butylammonium, tributyl-methylphosphonium, tetra-phenylphosphonium, diethyl-methylsulfonium, S-ethyl-N,N,N',N'-tetramethylisothiouronium, 1-allyl-3-methylimidazolium, 1-allyl-2,3-dimethylimidazolium, 1-cyanomethyl-3-methylimidazolium, 1-methyl-3-propinylimidazlium, 1,1-dimethylpyrrolidinium or trimethylsulfonium.

It goes without saying to the person skilled in the art that substituents, such as, for example, C, H, N, O, Cl, F, in the compounds according to the invention may be replaced by the corresponding isotopes.

Compounds of formula I in which [Kt]$^{z+}$ is Li$^+$ can be preferably used as conductive salts in primary batteries, secondary batteries, capacitors, supercapacitors or electrochemical cells, optionally also in combination with further conductive salts and/or additives, as constituent of a polymer electrolyte or phase-transfer medium.

Compounds of formula I in which [Kt]$^{z+}$ is Na$^+$ or K$^+$ can be preferably used as starting materials for compounds of formula I in which [Kt]$^{z+}$ is an organic cation or another inorganic cation than sodium or potassium.

Compounds of formula I in which [Kt]$^{z+}$ corresponds to formula (2), (5), (6), (9), tritylium, pyrylium, 1-benzopyrylium or 2-benzopyrylium as described above or preferably described above are preferably used as cationic polymerization initiator, photo-polymerization initiator or photo-acid generator. Particularly preferred organic cations to be used for this technical application corresponds to triarylsulfonium- or diaryliodonium cations in which aryl is defined as described above for the cations of formula (9).

Very particularly preferred organic cations to be used for this technical application as cationic polymerization initiator, photo-polymerization initiator or photo-acid generator are triphenylsulfonium, tritolylsulfonium, p-(tert-butyl)phenyl-diphenylsulfonium, p-methoxyphenyl-diphenylsulfonium, p-C$_6$H$_{13}$S-phenyl-diphenylsulfonium, m- or (p-C$_6$H$_5$S-phenyl)-diphenylsulfonium, tri[4-(4-acetyl-phenylsulfanyl)phenyl]sulfonium, tri(4-tert.-butylphenyl)sulfonium, diphenyliodonium, ditolyliodonium, phenyltolyliodonium, di(p-tert-butylphenyl)iodonium, m- or (p-C$_6$H$_5$S-phenyl)-phenyliodonium or tolyl-(4-sec.-butylphenyl) iodonium.

In addition, the invention relates to a process for the preparation of a compound of formula I as described before in which [Kt]$^{z+}$ is an alkali metal cation and z denotes 1 which denotes a compound of formula I-1 including sodium hydrido-tricyano-borate and potassium hydrido-tricyano-borate,

$$[Me]^+[BH(CN)_3]^- \qquad\qquad \text{I-1}$$

comprising in step 1 the reaction of a compound of formula II

$$[Me^1]^+[B(CN)_4]^- \qquad\qquad \text{II}$$

with an alkali metal [Me],
where [Me$^1$]$^+$ in formula II denotes an alkali metal cation which is different or equal to the alkali metal [Me] resulting in the formation of a compound of formula III

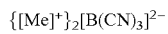

$$\{[Me]^+\}_2[B(CN)_3]^{2-} \qquad\qquad \text{III}$$

in which [Me]$^+$ denotes the alkali metal cation of the alkali metal and comprising in step 2 the hydrolysis of the compound of formula III resulted from step 1.

Compounds of formula II are commercially available e.g. from Merck KGaA, Darmstadt or can be synthesized according to WO 2004/072089, especially as disclosed in examples 1 to 3.

Alkali metals are commercially available materials.

[Me]$^+$ is preferably K$^+$ or Na$^+$, especially preferably K$^+$. [Me] is preferably lithium, sodium, potassium or their mixtures, especially preferably sodium.

The process for the preparation of compounds of the formula I in which [Kt]$^{z+}$ is an alkali metal cation and z denotes 1 which denotes a compound of formula I-1 as described above is carried out in liquid ammonia or in organic solvents which are inert to alkali metals, for example tetrahydrofuran, dialkyl ethers or amide-based solvents. If reaction proceeds in organic solvent the application of some catalysts, for example benzophenone, can accelerate the process and improve the yield of compounds of formula III.

Useful amide solvents are N,N-dimethylformamide, N,N-dimethylacetamide, N-methylpyrrolidone or HMPT (hexamethylphosphortriamide).

Liquid ammonia is condensed at temperatures around −78° C. and the reaction mixture is warmed up to a temperature between −50° C. to −30° C. in the presence of an inert atmosphere, like nitrogen or argon followed by warming up to 10° C. to 30° C. and evaporation of ammonia.

The hydrolysis of step 2 is preferably carried out in water at temperatures between 15° C. and 30° C., preferably at room temperature, in the absence or in the presence of an inorganic base such as alkali metal carbonates or acetates, or organic bases, preferably trialkylamines.

It is preferable to purify the compounds of formula I-1 by extraction with an organic solvent.

Useful organic solvents are for example, acetonitrile, dimethoxyethane, diglyme, tetrahydrofurane, or methyl-tert-butyl ether.

In addition, the invention relates to a special process for the preparation of a compound of formula I as described above in which [Kt]$^{z+}$ is the cation of potassium and z denotes 1 which denotes a compound of formula I-2

$$[K]^+[BH(CN)_3]^- \qquad\qquad \text{I-2}$$

comprising the reaction of a compound of formula IV

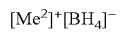    IV in which [Me²]⁺ denotes an alkali metal cation
with {4KSCN+K₂[Zn(SCN)₄]} and purification from minor amounts of the optional side product K[BH₂(CN)₂].

The reaction is carried out in a solid state reaction in inert atmosphere (nitrogen or argon) at temperatures between 100° C. to 220° C., preferably at 150° C. to 200° C., especially preferably at 185° C.

After cooling to room temperature, the mixture is dissolved in water and purified according to known methods in the art such as extraction methods.

The complex of rhodanid salts can be prepared from commercially available sodium or potassium rhodanid and zinc sulfate.

[Me²]⁺ is preferably K⁺ or Na⁺, especially preferably Na⁺. Sodium and potassium tetrahydridoborate is commercially available.

In addition, the invention relates to a process for the preparation of a compound of formula I as described above in which [Kt]$^{z+}$ is an alkali metal cation and z denotes 1 comprising the reaction of a compound of formula II

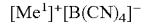    II with a strong base, preferably an alkali metal hydroxide, an alkali metal amide, a substituted amide or alkali metal alcoholate, where [Me¹]⁺ in formula II denotes an alkali metal cation which is different or equal to the alkali metal cation of the alkali metal hydroxide, alkali metal amide or alkali metal alcoholate. The alkali metal hydroxide is especially preferably used as strong base in the reaction with compounds of formula II.

The reaction is carried out without solvent or in the presence of an organic solvent at a temperature between 20° C. and 200° C., preferably at 50° C. to 200° C., preferably at 100° to 160° C.

Useful organic solvents are for example acetonitrile, dimethoxyethane, diglyme, tetrahydrofurane or methyl-tert-butyl-ether or amide solvents, like N,N-dimethylformamide, N,N-dimethylacetamide, N-methylpyrrolidone or HMPT (hexamethylphosphortriamide).

The process for the preparation of compounds of formula I in which the cation is an organic cation or an inorganic cation other than an alkalimetal cation is a metathesis reaction (salt-exchange reaction) in which the cation will be replaced as commonly known.

The invention therefore also relates to a process for the preparation of a compound of formula I according to one or more of claims 1 to 3 in which [Kt]$^{z+}$ is another cation than the used alkali metal cation in the starting material and z is 1, 2, 3 or 4 including sodium hydrido-tricyano-borate, potassium hydrido-tricyano-borate and silver hydrido-tricyano-borate in a salt-exchange reaction, characterized in that an alkali metal salt of formula I-1

    I-1 in which [Me]⁺ is an alkali metal cation or H[BH(CN)₃] is reacted with a compound of formula V

    V, in which
Kt has a meaning of an organic cation or inorganic cation other than the alkali metal cation of the compound of formula I-1 or H⁺ and
A denotes F⁻, Cl⁻, Br⁻, I⁻, OH⁻, [HF₂]⁻, [CN]⁻, [SCN]⁻, [R₁COO]⁻, [R₁OC(O)O]⁻, [R₁SO₃]⁻, [R₂COO]⁻, [R₂SO₃]⁻, [R₁OSO₃]⁻, [PF₆]⁻, [BF₄]⁻, [HSO₄]¹⁻, [SO₄]²⁻, [NO₃]⁻, [(R₂)₂P(O)O]⁻, [R₂P(O)O₂]²⁻, [(R₁O₂P(O)O]⁻, [(R₁O)P(O)O₂]²⁻, [(R₁O)R₁P(O)O]⁻, tosylate, malonate which may be substituted by straight-chain or branched alkyl groups having 1 to 4 C atoms, [HOCO₂]⁻ or [CO₃]²⁻, with the proviso that [SO₄]²⁻ and [CO₃]²⁻ are used merely for the synthesis of compounds of formula I having another metal cation than the alkali metal cation of the compound of formula I-1,
in which R₁ is each independently of another a straight-chain or branched alkyl group having 1 to 12 C atoms and
R₂ is each independently of one another a straight-chain or branched perfluorinated alkyl group having 1 to 12 C atoms and where electroneutrality should be taken into consideration in the formula of the salt KtA.

R₂ is particularly preferred trifluoromethyl, pentafluoroethyl or nonafluorobutyl, very particularly preferred trifluoromethyl or pentafluoroethyl.

R₁ is particularly preferred methyl, ethyl, n-butyl, n-hexyl or n-octyl, very particularly preferred methyl or ethyl.

Compounds of formula I-1, as described above, are preferably used in the metathesis reaction as described above.

Substituted malonates are for example methyl malonate or ethyl malonate.

The compounds of formula V are in most cases commercially available or can be synthesised by known processes. Known processes for the preparation of compounds of formula V are described, for example, in P. Wasserscheid, T. Welton (Eds.), Ionic Liquids in Synthesis, Second Edition, WILEY-VCH, Weinheim, 2008.

The anion in the formula V is preferably OH⁻, Cl⁻, Br⁻, I⁻, [HF₂]⁻, [CN]⁻, [SCN]⁻, [CH₃OC(O)O]⁻, [CH₃C(O)O]⁻, [CH₃SO₃]⁻, [CF₃C(O)O]⁻, [CF₃SO₃]⁻, [CH₃OSO₃]⁻, [SiF₆]²⁻, [PF₆]⁻, [BF₄]⁻, [HSO₄]¹⁻, [NO₃]⁻, [C₂H₅OSO₃]⁻, [(C₂F₅)₂P(O)O]⁻, [C₂F₅P(O)O₂]²⁻, tosylates, malonates or [SO₄]²⁻ and [CO₃]²⁻ with the proviso that [SO₄]²⁻ and [CO₃]⁻ are used merely for the synthesis of compounds of formula I having another metal cation than the alkali metal cation of the compound of formula I-1, particularly preferably OH⁻, Cl⁻, Br⁻, I⁻, [CH₃SO₃]⁻, [CH₃OSO₃]⁻, [PF₆]⁻, [CF₃COO]⁻, [CF₃SO₃]⁻, [(C₂F₅)₂P(O)O]⁻ or [CO₃]²⁻.

The anion in the formula V is very particularly preferably OH⁻, Cl⁻, Br⁻, [CH₃OSO₃]⁻, [CF₃SO₃]⁻, [CH₃SO₃]⁻ for the synthesis of compounds of formula I having an inorganic cation and the anion in the formula V is very particularly preferably OH⁻, Cl⁻, Br⁻, [CH₃OSO₃]⁻, [PF₆]⁻, [CF₃SO₃]⁻, [CH₃SO₃]⁻ or [(C₂F₅)₂P(O)O]⁻ for the synthesis of compounds of formula I having an organic cation.

Suitable organic salts for the preparation of the compounds of the formula I in which [Kt]$^{z+}$ is an organic cation are salts with cations of formula (1) to (8) or their preferred embodiments together with anions as defined as A described above or its preferred embodiments which means salts of cations of formulae (1) to (8) or their preferred embodiments and OH⁻, Cl⁻, Br⁻, [CH₃OSO₃]⁻, [PF₆]⁻, [CF₃SO₃]⁻, [CH₃SO₃]⁻ or [(C₂F₅)₂P(O)O]⁻.

Suitable substance for the preparation of the compound of the formula I in which [Kt]$^{z+}$ is H⁺ are aqueous H[BF₄] and H[PF₆] or H[BF₄] and H[PF₆] in organic solvents, preferably in diethylether. Reaction of K[BH(CN)₃] or Na[BH(CN)₃] with H[BF₄] or H[PF₆] results in the formation of H[BH(CN)₃] in solvated form and purely soluble potassium or sodium hexafluorophosphate or tetrafluoroborate.

Suitable inorganic salts for the preparation of the compounds of the formula I in which [Kt]$^{z+}$ is a metal cation e.g. from the group silver, magnesium, copper, zinc and calcium are, for example, Ag₂O, Ag₂CO₃, MgCO₃, CuO, ZnO, Zn[HCO₃]₂, CaCO₃ or Ca(OC(O)CH₃)₂. Useful salts for metathesis reaction to another alkali metal salt of formula I than potassium are e.g. LiBF$_4$.

The reaction is advantageously carried out in water in the case of the compounds of formula I-1 or in organic solvent, where temperatures of 10°-100° C., preferably 15°-60° C., particularly preferably room temperature, are suitable.

However, the reaction can alternatively also be carried out for the compounds of formula I in organic solvents at temperatures between 10° and 100° C. Suitable solvents here are acetonitrile, dialkylethers, tetrahydrofurane, dioxane, dichloromethane, dimethoxyethane or an alcohol, for example methanol, ethanol or iso-propanol.

The present invention furthermore relates to compounds of formula III

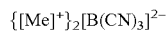    III in which [Me]$^+$ denotes an alkali metal cation, which is preferably Li$^+$, Na$^+$ or K$^+$.

The present invention furthermore relates to the corresponding process for the preparation of a compound of formula III as described above comprising the reaction of a compound of formula II

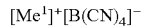    II in which [Me$^1$]$^+$ denotes an alkali metal cation with an alkali metal [Me$^1$] in which the alkali metal [Me$^1$] and the alkali metal cation [Me$^1$]$^+$ are the same or different.

The reaction above is carried out in liquid ammonia or in organic solvents which are inert to alkali metals, for example tetrahydrofuran, dialkyl ethers or amide-based solvents. Liquid ammonia is condensed at temperatures around −78° C. and the reaction mixture is warmed up to a temperature between −50° C. to −30° C. in the presence of an inert atmosphere, like nitrogen or argon followed by warming up to 10° C. to 30° C. and evaporation of ammonia.

The salts Na$_2$[B(CN)$_3$], Li$_2$[B(CN)$_3$] and K$_2$[B(CN)$_3$] are very moisture sensitive compounds, but they can be stored in the glove-box for a long time. These salts are soluble in liquid ammonia, dimethylformamide, slightly soluble in acetonitrile and NH$_2$CH$_2$CH$_2$NH$_2$. They are insoluble in tetrahydrofuran and diethylcarbonate.

The invention furthermore relates to the use of compounds of formula III as described above for the introduction of B(CN)$_3$-groups in chemical substances via reaction with electrophiles.

The present invention furthermore relates to the use of the compounds of formula I as described above as media for chemical reactions, as catalyst and/or as media in catalytical processes, as conducting salts, as components of electrolytes for the application in electrochemical cells, as components of supporting electrolytes for electrochemical processes, as surfactants, as phase-transfer catalysts, as trainer, as extractant; as antistatic additive, as plasticiser; as heat-transfer-medium, as modifier for membranes and textile materials; as lubricant, as additive to lubricant compositions or to another engineering fluids; as hydraulic fluid or as additive to hydraulic fluids.

Preferably, compounds of formula I having inorganic cations as described above are useful as catalyst, as conducting salts, as components of electrolytes for the application in electrochemical cells, as components of supporting electrolytes for electrochemical processes, as surfactants, as phase-transfer catalysts or as antistatic additive.

Preferably, compounds of formula I having organic cations as described above or H$^+$ are useful as media for chemical reactions, as catalyst and/or as media in catalytical processes, as conducting salts, as components of electrolytes for the application in electrochemical cells, as components of supporting electrolytes for electrochemical processes, as surfactants, as phase-transfer catalysts, as trainer, as extractant; as antistatic additive, as plasticiser; as heat-transfer-medium, as modifier for membranes and textile materials; as lubricant, as additive to lubricant compositions or to another engineering fluids; as hydraulic fluid or as additive to hydraulic fluids.

In the case of the use of the said organic salts of formula I as media in catalytical processes or as solvents, these are suitable in any type of reaction known to the person skilled in the art, for example for transition-metal- or enzyme-catalysed reactions, such as, for example, hydroformylation reactions, oligomerisation reactions, esterifications or isomerisations, where the said list is not exhaustive.

On use as extractant, the organic salts of formula I can be employed to separate off reaction products, but also to separate off impurities, depending on the solubility of the respective component in the ionic liquid. In addition, the ionic liquids may also serve as separation media in the separation of a plurality of components, for example in the distillative separation of a plurality of components of a mixture.

Further possible applications are use as plasticiser in polymer materials and as conductive salt or additive in various electrochemical cells and applications, for example in galvanic cells, in capacitors or in fuel cells.

Further fields of applications of the organic salts of formula I, according to this invention are solvents for carbohydrate containing solids in particular biopolymers and derivatives or degradation products thereof. In addition, these new compounds can be applied as lubricants, working fluids for maschines, such as compressors, pumps or hydraulic devices. A further field of application is the field of particle or nanomaterial synthesis where these ionic liquids can act as medium or additive.

The compounds of formula I in which [Kt]$^{z+}$ corresponds to formula (2), (5), (6), (9), tritylium, pyrylium, 1-benzopyrylium or 2-benzopyrylium as described above or preferably described above are preferably used as cationic polymerization initiator, photo-polymerization initiator or photo-acid generator.

A cationic polymerization initiator is able to start the polymerization of at least one monomer, for example the polymerization of cationic polymerizable compounds such as iso-butylene, styrene, vinylethers, lactones, lactames, cyclic ethers or epoxy-containing compounds.

The process of polymerization is started via radiation in case a photo-polymerization initiator is used which means that the mixture of photo-initiator and at least one monomer is irradiated through energetic rays such as light, electrons or gamma rays. This kind of photo-polymerization normally leads especially to quickly crosslinked end products. The compounds of formula I with cations of formula (2), (5), (6), (9), tritylium, pyrylium, 1-benzopyrylium or 2-benzopyrylium as described above are cationic photo-polymerization initiators. Particularly, compounds of formula I with cations of formula (2) and (9) are preferred.

Photo-polymerization initiators are often components of formulations of lacquers or resins which often need a curing in fractional amounts of seconds. The curing may be initiated through light, laser, electrons or gamma rays, especially through UV-light.

Photo-polymerization is often used in various technical applications for example for curing a coating film, forming a planographic printing plate, a resin letterpress printing plate and a printed circuit board, preparing a photoresist and a photomask, and making a black-and-white or color transfer sheet and a coloring sheet.

In case the compounds of formula I with cations of formula (2), (5), (6), (9), tritylium, pyrylium, 1-benzopyrylium or 2-benzopyrylium are irradiated with light, laser, electrons or gamma rays, they are able to build the corresponding Brønsted acid or Lewis acid on spot which means in a catalytic amount and are therefore able to start the polymerization through this acid. Such compounds which show such a property are commonly known as photo-acid generator (PAG). PAG's are highly active and have been shown to catalyze the deprotection of acid-sensitive organic functional groups with good photospeeds. PAG's are very often used in resists.

Another object of the invention is therefore a curable composition comprising at least one compound of formula I with cations of formula (2), (5), (6), (9), tritylium, pyrylium, 1-benzopyrylium or 2-benzopyrylium as described before and at least one polymerizable compound.

Another object of the invention is therefore a curable composition comprising at least one compound of formula I with cations of formula (2) and (9) as described or preferably described before and at least one polymerizable compound.

The compounds of formula I with organic cations, e.g. ionic liquids according to this invention may be preferably used in electrochemical and/or optoelectronic devices, especially in electrolyte formulations.

The present invention therefore relates furthermore to an electrolyte formulation comprising at least one compound of formula I as described above or preferably described.

Electrolyte formulations comprising compounds of formula I in which $[Kt]^{z+}$ is an organic cation can be preferably used in electrochemical cells, optionally also in combination with further conductive salts and/or additives, as constituent of a polymer electrolyte or phase-transfer medium.

Electrolyte formulations comprising compounds of formula I can be preferably used in electrochemical and/or optoelectronic devices such as a photovoltaic cell, a light emitting device, an electrochromic or photo-electrochromic device, an electrochemical sensor and/or biosensor, particularly preferred in a dye sensitised solar cell.

Such electrolyte formulations form a crucial part of the disclosed devices and the performance of the device largely depends on the physical and chemical properties of the various components of these electrolytes.

Factors which are still impeding the technical application of many electrochemical and/or optoelectronic devices and in particular of dye or quantum dot sensitized solar cells, are reliability problems caused by the volatility of organic solvents based electrolytes. It is very difficult to maintain a tight sealing of the electrolyte in e.g. a DSC panel, which has to withstand the temperature differences of daily day-night cycles and the concomitant thermal expansion of the electrolyte. The abbreviation DSC means dye sensitized solar cell. This problem can be solved in principle by the use of ionic liquid-based electrolytes. For review "Ionic liquid electrolytes for dye-sensitized solar cells" see: William R Pitner et al., "Application of Ionic Liquids in Electrolyte System" *Green Chemistry*. vol. 6, (2010).

Ionic liquids or liquid salts are typically ionic species which consist of an organic cation and a generally inorganic anion usually having melting points below 373 K. Various binary ionic liquid electrolytes have recently been applied to dye-sensitized solar cells. WO 2007/093961 and WO 2009/083901 describe so far the best power conversion efficiencies in ionic liquid-based electrolytes for DSC containing a significant quantity of organic salts with tetracyanoborate (TCB) anions.

Electrolyte formulations according to the invention are alternatives to already known electrolyte formulations. They show especially in the field of electrolyte formulations of dye sensitised solar cells a good performance particularly under high temperature. The advantage of the use of compounds of formula I having an organic cation and a hydridotricyano-borate anion is their low viscosity and high thermal stability.

In chemistry, an electrolyte is any substance containing free ions that make the substance electrically conductive. The most typical electrolyte is an ionic solution, but molten electrolytes and solid electrolytes are also possible. An electrolyte formulation according to the invention is therefore an electrically conductive medium, basically due to the presence of at least one substance that is present in a dissolved and or in molten state and undergo dissociation into ionic species, i.e. supporting an electric conductivity via motion of ionic species. However, the said electric conductivity may not be of the major relevance to the role of the electrolyte of a dye-sensitised solar cell. Therefore, the scope of this invention is not limited to highly conductive electrolyte media.

The term electrolyte may be used for the term electrolyte formulation as well comprising all ingredients as disclosed for the electrolyte formulation.

The electrolyte formulations according to the invention may include or comprise, essentially consist of or consist of the said necessary or optional constituents. All compounds or components which can be used in the agents or compositions are either known and commercially available or can be synthesized by known processes.

Typical molar concentrations of the hydridotricyanoborate compound in the electrolyte formulations range from 0.1 to 5.5 M, preferably from 0.8 to 3.5 M. This molar concentration in the electrolyte may be achieved with one or more compounds of formula I in which $Kt^{z+}$ has a meaning as described or preferably described above.

Preferably, the molar concentration is achieved with at least one compound of formula I as described or preferably described above.

For the purpose of the present invention, the molar concentration refer to the concentration at 25° C.

The present invention relates furthermore to an electrolyte formulation comprising at least one compound of formula (1) as described above or preferably described together with redox active species such as iodide/tri-iodide, Ferrocene derivatives or Co(II)/Co(III) complexe couples such as Co(II)/Co(III)(dbbip)$_2$ in which dbbip means 2,6-bis(1'-butylbenzimidazol-2'-yl)pyridine, Co(II)/Co(III)(bpy)$_3$ where bpy denotes bipyridine or alkylated bipyridine derivates thereof, Co(II)/Co(III)(dmb)$_3$ where dmb denotes 4,4'-dimethyl-2,2'-bipyridine, Co(II)/Co(III)(dtb)$_3$ where dtb denotes 4,4'-di-tert-butyl-2,2'-bipyridine, Co(II)/Co(III)(phen)$_3$ where phen denotes 1,10-phenanthroline, preferably a redox couple of iodine and at least one iodide salt.

The electrolyte formulation of the invention preferably comprises iodine ($I_2$). Preferably, it comprises from 0.0005 to 7 mol/dm$^3$, more preferably 0.01 to 5 mol/dm$^3$ and most preferably from 0.05 to 1 mol/dm$^3$ of $I_2$.

The iodide salt consists of an inorganic or organic cation and I$^-$ as anion. There exists no limitation to the kind of cation. However, to limit the amount of different cations in the electrolyte formulations, especially for DSC, organic cations shall be used as already described for the compounds of formula I. Preferably, the electrolyte formulation comprises at least one iodide salt in which the organic cation is independently selected from the group of

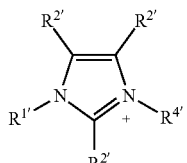     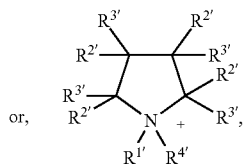

imidazolium           pyrrolidinium in which the substituents $R^{2'}$ and $R^{3'}$ each, independently of one another, denote H or straight-chain or branched alkyl having 1 to 20 C atoms, $R^{1'}$ and $R^{4'}$ each, independently of one another, denote straight-chain or branched alkyl having 1-20 C atoms, which optionally may be partially fluorinated or perfluorinated, straight-chain or branched alkenyl having 2-20 C atoms and one or more double bonds, which optionally may be partially fluorinated,
straight-chain or branched alkynyl having 2-20 C atoms and one or more triple bonds, which optionally may be partially fluorinated.

Particularly preferred examples of the at least one iodide salt are 1-ethyl-3-methylimidazolium iodide (emim I), 1-propyl-3-methylimidazolium iodide (pmim I), 1-butyl-3-methyl-imidazolium iodide (bmim I), 1-hexyl-3-methylimidazolium iodide (hmim I), 1,3-dimethyl-imidazolium iodide (mmim I), 1-allyl-3-methylimidazolium iodide (amim I), N-butyl-N-methyl-pyrrolidinium iodide (bmpl I) or N,N-dimethyl-pyrrolidinium iodide (mmpl I).

Other components of the electrolyte formulation are one or several further salts, solvents, and others, as indicated further below.

If the electrolyte formulation is a binary system, it comprises two salts, one further salt or iodide salt and a compound of formula I as described above. If the electrolyte formulation is a ternary system, it comprises two further salts and/or iodide salts and a compound of formula I as described above. The binary system comprises 90-10 weight %, preferably 70-30 weight %, more preferably 55-40 weight % of the further salt or iodide salt and 10-90 weight %, preferably 30-70 weight % or more preferably 45-60 weight % of the compound of formula I as described above. The percentages in this paragraph are expressed with respect to the total of salts (=100 weight %) present in the electrolyte formulation according to the invention. Amounts of further, generally optional components (additives) indicated below, such as N-containing compounds having unshared electron pairs, iodine, solvents, polymers, and nanoparticles, for example, are not considered therein. The same percentages apply to ternary or quaternary systems which means the total of the further salts has to be used in the given ranges, e.g. two further ionic liquids are comprised in e.g. 90-10 weight. % in the electrolyte formulation according to the invention.

According to another embodiment of the present invention, the electrolyte formulation comprises at least one further salt with organic cations comprising a quaternary nitrogen and an anion selected from a halide ion, such as F⁻, Cl⁻, a polyhalide ion, a fluoroalkanesulfonate, a fluoroalkanecarboxylate, a tris(fluoroalkylsulfonyl)methide, a bis(fluoroalkylsulfonyl)imide, bis(fluorosulfonyl)imide, a nitrate, a hexafluorophosphate, a tris-, bis- and mono-(fluoroalkyl)fluorophosphate, a tetrafluoroborate, a dicyanamide, a tricyanomethide, a tetracyanoborate, a thiocyanate, an alkylsulfonate or an alkylsulfate, with fluoroalkane-chain having 1 to 20 C atoms, preferably perfluorinated, fluoroalkyl having 1 to 20 C atoms and alkyl having 1 to 20 C atoms. Fluoroalkane-chain or fluoroalkyl is preferably perfluorinated.

Preferably, the further salts are selected from salts comprising anions such as thiocyanate, tetracyanoborate and/or bis(fluorosulfonyl)imide, particularly preferred further salts are tetracyanoborates.

The cation of the at least one further salt or of a preferred further salt may be selected amongst organic cations as defined above for the compounds of formula I including also the preferred meanings.

In another embodiment of the invention, guanidinium thiocyanate may be added to the electrolyte formulation according to the invention.

In a preferred embodiment, the electrolyte formulation of the present invention further comprises at least one compound containing a nitrogen atom having non-shared electron pairs. Examples of such compounds are found in EP 0 986 079 A2, starting on page 2, lines 40-55, and again from page 3, lines 14 extending to page 7, line 54, which are expressly incorporated herein by reference. Preferred examples of compounds having non-shared electron pairs include imidazole and its derivatives, particularly benzimidazole and its derivatives.

The electrolyte formulation of the present invention may comprise an organic solvent. Preferably, the electrolyte formulation comprises the compound comprising a hydridotricyanoborate anion in the range between 5% to 70% and the organic solvent in the range between 70% to 0% based on the total weight of the formulation. Particularly preferably, the electrolyte formulation comprises less than 50% of an organic solvent or less than 40%, more preferably less than 30%, still more preferably less than 20% and even less than 10%. Most preferably, the electrolyte formulation comprises less than 5% of an organic solvent. For example, it is substantially free of an organic solvent. Percentages are indicated on the basis of weight %.

Organic solvents, if present in such amounts as indicated above, may be selected from those disclosed in the literature. Preferably, the solvent, if present, has a boiling point higher than 160 degrees centigrade, more preferably higher than 190 degrees such as propylene carbonate, ethylene carbonate, butylene carbonate, gamma-butyrolactone, gamma-valerolactone, glutaronitrile, adiponitrile, N-methyloxazolidinone, N-methylpyrrolidinone, N,N'-dimethylimidazolidinone, N,N-dimethylacetamide, cyclic ureas preferably 1,3-dimethyl-2-imidazolidinone or 1,3-dimethyl-3,4,5,6-tetrahydro-2(1H)-pyrimidinone, glymes preferably tetraglyme, sulfolane, sulfones which are preferably asymmetrically substituted such as 2-ethanesulfonyl-propane, 1-ethanesulfonyl-2-methyl-propane or 2-(propane-2-sulfonyl)-butane, 3-methylsulfolane, dimethylsulfoxide, trimethylphosphate and methoxy-substituted nitriles. Other useful solvents are acetonitrile, benzonitrile and or valeronitrile. Preferred organic solvents are gamma-butyrolactone and tetraglyme.

If a solvent is present in the electrolyte formulation, there may further be comprised a polymer as gelling agent, wherein the polymer is polyvinylidenefluoride, polyvinylidene-hexafluoropropylene, polyvinylidene-hexafluoropropylene-chlorotrifluoroethylene copolymers, nafion, polyethylene oxide, polymethylmethacrylate, polyacrylonitrile, polypropylene, polystyrene, polybutadiene, polyethyleneglycol, polyvinylpyrrolidone, polyaniline, polypyrrole, polythiophene. The purpose of adding these polymers to electrolyte formulations is to make liquid electrolytes into quasi-solid or solid electrolytes, thus improving solvent retention, especially during aging.

The electrolyte formulation of the invention may further comprise metal oxide nanoparticles like $SiO_2$, $TiO_2$, $Al_2O_3$, MgO or ZnO, for example, which are also capable of increasing solidity and thus solvent retention.

The electrolyte formulation of the invention has many applications. For example, it may be used in an optoelectronic and/or electrochemical device such as a photovoltaic cell, a light emitting device, an electrochromic or photo-electrochromic device, an electrochemical sensor and/or biosensor.

The present invention therefore relates further to the use of the electrolyte formulation as described in detail above in an electrochemical and/or optoelectronic device which is a photovoltaic cell, a light emitting device, an electrochromic or photo-electrochromic device, an electrochemical sensor and/or biosensor. Preferably, the electrolyte formulation may be used in dye sensitized solar cells.

The present invention therefore relates furthermore to an electrochemical and/or optoelectronic device which is a photovoltaic cell, a light emitting device, an electrochromic or photo-electrochromic device, an electrochemical sensor and/or biosensor comprising an electrolyte formulation comprising at least one compound of formula I as described or preferably described above.

Preferably, the compound of formula I is a compound of formula I in which $[Kt]^{z+}$ is an organic cation as described above including all preferred meanings for application in dye-sensitized solar cells.

According to a preferred embodiment, the device of the present invention is a dye or quantum dot sensitized solar cell, particularly preferably a dye sensitized solar cell.

Quantum dot sensitized solar cells are disclosed in U.S. Pat. No. 6,861,722, for example. In dye-sensitized solar cells, a dye is used to absorb the sunlight to convert into the electrical energy. There are no restrictions per se with respect to the choice of the dye as long as the LUMO energy state is marginally above the conduction bandedge of the photoelectrode to be sensitized. Examples of dyes are disclosed in EP 0 986 079 A2, EP 1 180 774 A2 or EP 1 507 307 A1.

Preferred dyes are organic dyes such as MK-1, MK-2 or MK-3 (its structures are described in FIG. 1 of N. Koumura et al, J. Am. Chem. Soc. Vol 128, no. 44, 2006, 14256-14257), D102 (CAS no. 652145-28-3), D-149 (CAS no. 786643-20-7), D205 (CAS no. 936336-21-9), D358 (CAS no. 1207638-53-6), YD-2 as described in T. Bessho et al, Angew. Chem. Int. Ed. Vol 49, 37, 6646-6649, 2010, Y123 (CAS no. 1312465-92-1), bipyridin-Ruthenium dyes such as N3 (CAS no. 141460-19-7), N719 (CAS no. 207347-46-4), Z907 (CAS no. 502693-09-6), C101 (CAS no. 1048964-93-7), C106 (CAS no. 1152310-69-4), K19 (CAS no. 847665-45-6), HRS-1 (CAS no. 906061-30-1 as disclosed in K. J. Jiang et al, Chem. Comm. 2460, 2006) or terpyridine-Ruthenium dyes such as N749 (CAS no. 359415-47-7).

The structure of D205 is

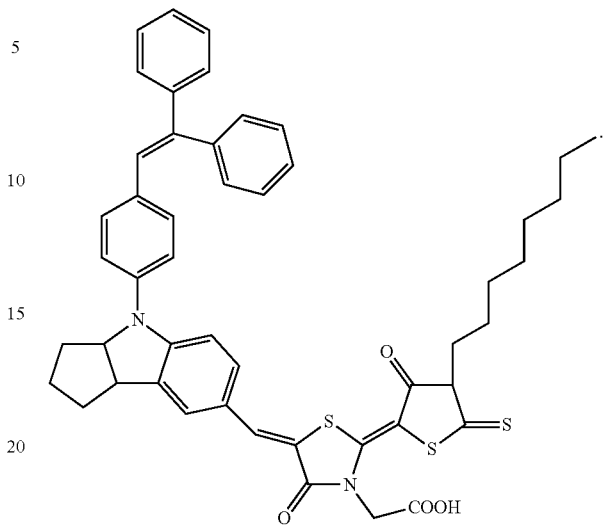

The structure of D358 is

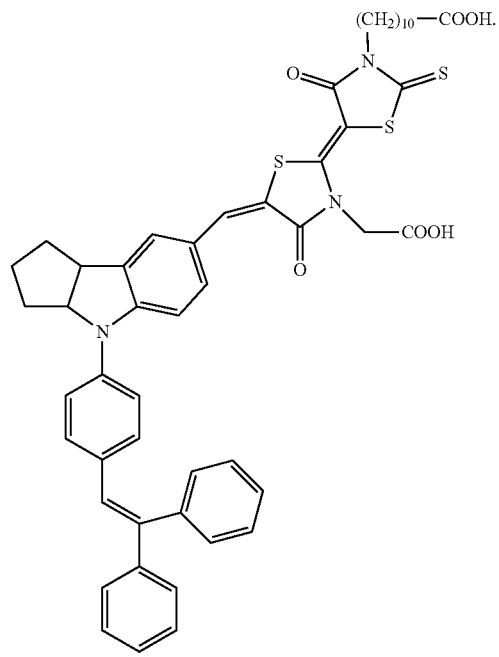

Particularly preferred dyes are Z907 or Z907Na which are both an amphiphilic ruthenium sensitizer, C106, D358 or HRS-1. The dye Z907Na means NaRu(2,2'-bipyridine-4-carboxylic acid-4'-carboxylate)(4,4'-dinonyl-2,2'-bipyridine)$(NCS)_2$.

Very particularly preferred dyes are Z907 or Z907Na and/or D358. Very very particularly preferred dyes are Z907 or Z907Na.

In a special embodiment, the dye is coadsorbed with a phosphinic acid. A preferred example of a phosphinic acid is bis(3,3-dimethyl-butyl)-phosphinic acid (DINHOP) as disclosed in M. Wang et al, Dalton Trans., 2009, 10015-10020.

For example, a dye-sensitized solar cell comprises a photo-electrode, a counter electrode and, between the photoelectrode and the counter electrode, an electrolyte formulation or a charge transporting material, and wherein a sensitizing dye is absorbed on the surface of the photo-electrode, on the side facing the counter electrode.

According to a preferred embodiment of the device according to the invention, it comprises a semiconductor, the electrolyte formulation as described above and a counter electrode.

According to a preferred embodiment of the invention, the semiconductor is based on material selected from the group of Si, $TiO_2$, $SnO_2$, $Fe_2O_3$, $WO_3$, ZnO, $Nb_2O_5$, CdS, ZnS, PbS, $Bi_2S_3$, CdSe, GaP, InP, GaAs, CdTe, $CuInS_2$, and/or $CuInSe_2$. Preferably, the semiconductor comprises a mesoporous surface, thus increasing the surface optionally covered by a dye and being in contact with the electrolyte. Preferably, the semiconductor is present on a glass support or plastic or metal foil. Preferably, the support is conductive.

The device of the present invention preferably comprises a counter electrode. For example, fluorine doped tin oxide or tin doped indium oxide on glass (FTO- or ITO-glass, respectively) coated with Pt, carbon of preferably conductive allotropes, polyaniline or poly(3,4-ethylenedioxythiophene) (PEDOT). Metal substrates such as stainless steel or titanium sheet may be possible substrates beside glass.

The device of the present invention may be manufactured as the corresponding device of the prior art by simply replacing the electrolyte by the electrolyte formulation of the present invention. For example, in the case of dye-sensitized solar cells, device assembly is disclosed in numerous patent literature, for example WO 91/16719 (examples 34 and 35), but also scientific literature, for example in Barbé, C. J., Arendse, F., Comte, P., Jirousek, M., Lenzmann, F., Shklover, V., Grätzel, M. J. Am. Ceram. Soc. 1997, 80, 3157; and Wang, P., Zakeeruddin, S. M., Comte, P., Charvet, R., Humphry-Baker, R., Grätzel, M. J. Phys. Chem. B 2003, 107, 14336.

Preferably, the sensitized semi-conducting material serves as a photo-anode. Preferably, the counter electrode is a cathode.

The present invention provides a method for preparing a photoelectric cell comprising the step of bringing the electrolyte formulation of the invention in contact with a surface of a semiconductor, said surface optionally being coated with a sensitizer. Preferably, the semiconductor is selected from the materials given above, and the sensitizer is preferably selected from quantum dots and/or a dye as disclosed above, particularly preferably selected from a dye.

Preferably, the electrolyte formulation may simply be poured on the semiconductor. Preferably, it is applied to the otherwise completed device already comprising a counter electrode by creating a vacuum in the internal lumen of the cell through a hole in the counter electrode and adding the electrolyte formulation as disclosed in the reference of Wang et al., J. Phys. Chem. B 2003, 107, 14336.

The present invention will now be illustrated, without limiting its scope, by way of the following examples. Even without further comments, it is assumed that a person skilled in the art will be able to utilise the above description in the broadest scope. The preferred embodiments and examples should therefore merely be regarded as descriptive disclosure which is absolutely not limiting in any way.

The substances are characterised by means of Raman and NMR spectroscopy and X-Ray analysis. The NMR-spectra are measured in deuterated solvents Aceton-$D_6$ or $CD_3CN$ by use of Bruker Avance III Spektrometer with Deuterium Lock. The resonance frequency for different nuclea are: $^1H$: 400.17 MHz, $^{11}B$: 128.39 MHz, $^{31}P$: 161.99 MHz und $^{13}C$: 100.61 MHz. The following references are used: TMS für $^1H$ und $^{13}C$ spectra and $BF_3.Et_2O$— for $^{11}B$ spectra.

EXAMPLES

Example 1

Potassium hydrido-tricyano-borate—$K[BH(CN)_3]$

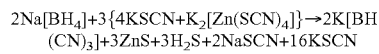

$$2Na[BH_4]+3\{4KSCN+K_2[Zn(SCN)_4]\} \rightarrow 2K[BH(CN)_3]+3ZnS+3H_2S+2NaSCN+16KSCN$$

The mixture of 1.08 g (28.5 mmol) $NaBH_4$ and 27 g (3.04 mol) $\{4KSCN+K_2[Zn(SCN)_4]\}$ is heated for 5 hours at 185° C. under vacuum. After cooling to room temperature, the reaction mixture is dissolved in 200 cm³ water and the precipitate of ZnS is filtered off. The solution is treated with 100 cm³ of 36%-ige HCl and water is distilled of in vacuum at 50-60° C. The residue is extracted with 250 cm³ of tetrahydrofuran and non-soluble precipitant is filtered off. The solvent is evaporated in vacuum and residue is dissolved in 100 cm³ of water. After filtration and treatment with 50 cm³ of 36%-ige HCl, the solution is evaporated in vacuum at 50-60° C. The residue is dissolved in 150 cm³ of acetonitrile. The solution is filtered and evaporated in vacuum. The residue is dissolved in 50 cm³ of 36%-ige HCl. The solution is left stirring for 12 hours and is evaporated in vacuum at 50-60° C. The residue is dissolved in 10 cm³ of water. The solution is neutralized with $K_2CO_3$ and filtered. The product is extracted from this solution with tetrahydrofuran (50+20+20 cm³). The THF solution is dried with $K_2CO_3$ and evaporated. The residue is dried in vacuum. 0.43 g of $K[BH(CN)_3]$ is obtained. The product contains of about 10-15% $K[BH_2(CN)_2]$.

Further purification can be achieved by treatment with 36%-ige HCl within 15 hours at 100° C. followed by extraction with acetonitrile.

$K[BH(CN)_3]$: a=4.0558(3), b=8.6645(5), c=9.3318(8) Å, α=104.127(7), β=100.542(7), γ=90.110(5)°, V=312.27, Z=2, P-1, t=150K.

Example 2

Potassium hydrido-tricyano-borate—$K[BH(CN)_3]$

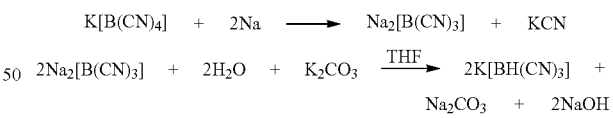

$$K[B(CN)_4] + 2Na \longrightarrow Na_2[B(CN)_3] + KCN$$
$$2Na_2[B(CN)_3] + 2H_2O + K_2CO_3 \xrightarrow{THF} 2K[BH(CN)_3] + Na_2CO_3 + 2NaOH$$

To 21.0 g (136 mmol) $K[B(CN)_4]$ and 6.3 g (274 mmol) of Na ca. 100 cm³ of liquid ammonia is condensed by cooling of the reaction vessel with dry ice (−78° C.). The reaction mixture is slowly warmed up to −40 to −30° C. (temperature in the cooling bath) until the exothermic reaction starts. The reaction mixture formed two phases: upper layer had deep-blue colour of the Na solution in $NH_3$; bottom layer had red-orange colour of $Na_2[B(CN)_3]$ in $NH_3$. Within 30-50 min the deep-blue colour practically completely disappeared. This indicated that reaction is completed. The reaction mixture is slowly warmed up in inert atmosphere (Ar) to the room temperature resulting in ammonia evaporation. The residue is pumped for ca. 10 min in vacuum (to remove the traces of ammonia) and treated with 100 cm³ of water. Within ca. 30 min at room temperature (if the traces of non-reacted Na is remained in the reaction mixture, the cooling of the reaction vessel is recommended) the yellow colour of solid $Na_2[B(CN)_3]$ disappeared and transparent colour-less solution in water is formed. The volume of the reaction mixture is reduced to 40-50 cm³. The residue is treated with 22 g $K_2CO_3$ and 100 cm³ of tetrahydrofurane (THF). The THF-phase is separated and the water phase is extracted two times with 50 cm³ of tetrahydrofurane. The combined THF-solution is dried with $K_2CO_3$, filtrated and the sovent is evaporated. The residue is washed with $CH_2Cl_2$ (2×50 cm³) and dried in vacuum. The yield of $K[BH(CN)_2]$ is 17.6 g (100%).

$^{11}$B-NMR: δ, ppm=−40.2 d, $^1J_{B,H}$=98 Hz.

$^1H\{^{11}B\}$-NMR (Solvent: Acetonitrile-$D_3$): δ, ppm=1.77 s (BH, 1H).

Raman-spectrum, ν, cm⁻¹, $K[HB(CN)_3]$:

2462 s, 2430 m, 2235 s, 2222 vs, 1058 w, 728 w, 522 w, 498 vw, 348 s, 180 s, 171s.

Example 3

Potassium hydrido-tricyano-borate—$K[BH(CN)_3]$

$K[B(CN)_4]+KOH.0.55H_2O \rightarrow K[BH(CN)_3]+KCN$

A mixture of 10 g (65 mmol) $K[B(CN)_4]$ and 22 g (334 mmol) $KOH.0.55H_2O$ in 20 cm³ of diglyme is stirred and heated for 80 min at 160-165° C. After cooling to room temperature the reaction mixture is dissolved in 40 cm³ of water and product is extracted with tetrahydrofuran (3×100 cm³). The THF-extract is dried with $K_2CO_3$, filtered and all volatile components of the mixture are removed in vacuum. The residue is treated with 100 cm³ of 36%-ige HCl and the solution is evaporated in vacuum at 50-60° C. The residue is dissolved in 50 cm³ of acetonitrile and 50 cm³ $CH_2Cl_2$ are added to this solution. The mixture is filtered and diluted with 450 cm³ of $CH_2Cl_2$. The precipitant ($K[BH(CN)_3]$ .x$CH_3CN$) is filtered off and washed with $CH_2Cl_2$. The product, $K[BH(CN)_3].xCH_3CN$, is dried in vacuum at 50° C. for 15 hours. Yield of solid $K[BH(CN)_3]$ is 6.0 g (72%).

The product is characterized by means of NMR spectroscopy. The $^{11}$B-NMR and $^1H\{^{11}B\}$-NMR spectra are identical to in Example 2 described spectra Example 4

Synthesis of $M_2[B(CN)_3]$, (M=Li, Na, K)

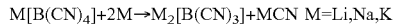

$M[B(CN)_4]+2M \rightarrow M_2[B(CN)_3]+MCN$  M=Li,Na,K 30 mmol of $M[B(CN)_4]$ (Merck KGaA, Darmstadt) and 60 mmol M (M=Li, Na or K) are placed into 100 cm³ glass flask under inert atmosphere (glove-box). Ca. 30 cm³ of liquid ammonia are condensed to this mixture by cooling of reaction vessel with dry ice (−78° C.). The temperature of the reaction mixture is slowly increased to −40° C. (temperature in the cooling bath) until an exothermal reaction was started. During the reaction the blue colour of alkalimetal solution in ammonia disappeared and yellow precipitant was formed from orange solution. The reaction time for K is of about 30 min; for Na is ca. 1 hour and for Li-2 hours. The side product, MCN, can be washed out with liquid ammonia (in the case of M=K or Na) at −78° C. or with tetrahydrofuran in the case of LiCN. The residue, practically pure $M_2[B(CN)_3]$, is dried in the vacuum at room temperature.

Raman-spectrum, ν, cm⁻¹:

$Na_2[B(CN)_3]$: 2105 vs, 2040 s, 2013 vs, 1993 vs, 1154 w, 1113 w, 577/552 m, 506 w, 174 vs $K_2[B(CN)_3]$: 2098 vs, 2040 s, 2022 vs, 1997 vs, 1137 w, 1115 w, 561/551 m, 502 w, 194 vs

NMR-spectra of $[B(CN)_3]^{2-}$ dianion (Solvent: $ND_3$, at −40° C.; Reference substance $K[B(CN)_4]$: $δ(^{11}B)$=−38.6 ppm and $δ(^{13}C)$=122.3 ppm):

NMR $^{11}$B, δ, ppm: −45.3, $^1J(^{11}B, ^{13}C)$=92 Hz

NMR $^{13}$C, δ, ppm: 157.7, $^1J(^{11}B, ^{13}C)$=93 Hz $K_2[B(CN)_3]$ is decomposed above 230° C. (DSC onset) exothermally with colouring (brown).

The yellow salts $M_2[B(CN)_3]$ hydrolyze quantitatively with water to the corresponding hydrido-tricyano borates, $M[BH(CN)_3]$ which can be isolated from aqueous solution as pure salts in quantitative yield.

$M_2[B(CN)_3]+H_2O \rightarrow M[HB(CN)_3]+MOH$ (M=Li,Na, K)

Example 5

1-ethyl-3-methylimidazolium hydrido-tricyano-borate—$[EMIM][BH(CN)_3]$

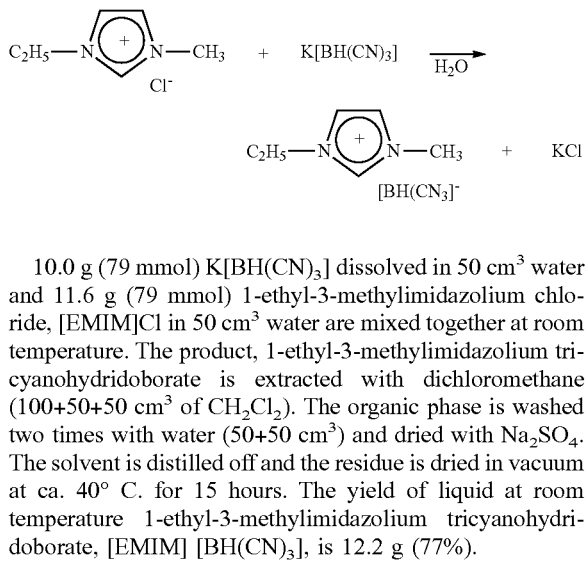

10.0 g (79 mmol) $K[BH(CN)_3]$ dissolved in 50 cm³ water and 11.6 g (79 mmol) 1-ethyl-3-methylimidazolium chloride, [EMIM]Cl in 50 cm³ water are mixed together at room temperature. The product, 1-ethyl-3-methylimidazolium tricyanohydridoborate is extracted with dichloromethane (100+50+50 cm³ of $CH_2Cl_2$). The organic phase is washed two times with water (50+50 cm³) and dried with $Na_2SO_4$. The solvent is distilled off and the residue is dried in vacuum at ca. 40° C. for 15 hours. The yield of liquid at room temperature 1-ethyl-3-methylimidazolium tricyanohydridoborate, [EMIM] $[BH(CN)_3]$, is 12.2 g (77%).

Residual water: 15 ppm.

Chloride impurities: 9 ppm (ion-chromatography)

Viscosity: 12.2 mPa·s (20° C.).

Decomposition temperature: above 277° C. (DSC/TGA; onset).

$^1H\{^{11}B\}$-NMR (Solvent: Acetonitrile-$D_3$): δ, ppm=1.49 t ($CH_3$, 3H), $^3J_{H,H}$=7.3 Hz; 1.77 s (BH, 1H); 3.86 s ($CH_3$, 3H); 4.20 q ($CH_2$, 2H), $^3J_{H,H}$=7.3 Hz; 7.36 d,d (CH, H); 7.42 d,d (CH, H), $^3J_{H,H}$=1.7 Hz; 8.46 br.s (CH, 1H).

$^{11}$B-NMR (Solvent: Acetonitrile-$D_3$): δ, ppm=−40.2 s, $^1J_{B,H}$=97 Hz.

Example 6

1-butyl-1-methylpyrrolidinium hydrido-tricyano-borate—[BMPL][BH(CN)$_3$]

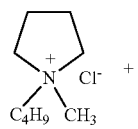 + K[BH(CN)$_3$] $\xrightarrow{H_2O}$ 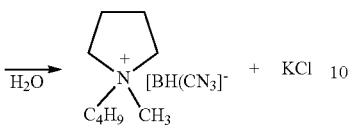 + KCl 7.3 g (57 mmol) K[BH(CN)$_3$] dissolved in 20 cm$^3$ water and 10.1 g (57 mmol) 1-butyl-1-methylpyrrolidinium chloride, [BMPL]Cl in 20 cm$^3$ water are mixed together at room temperature. The product, 1-butyl-1-methylpyrrolidinium tricyanohydridoborate, is extracted with dichloromethane (100+50+50 cm$^3$ of CH$_2$Cl$_2$). The organic phase is washed two times with water (50+50 cm$^3$) and dried with Na$_2$SO$_4$. The solvent is distilled off and the residue is dried in vacuum at ca. 45° C. for 16 hours. The yield of liquid at room temperature 1-butyl-1-methylpyrrolidinium tricyanohydridoborate, [BMPL][BH(CN)$_3$], is 12.6 g (96%).

$^1$H{$^{11}$B}-NMR (Solvent: Acetonitrile-D$_3$): δ, ppm=0.98 t (CH$_3$, 3H), $^3J_{H,H}$=7.3 Hz; 1.40 t.q (CH$_2$, 2H), $^3J_{H,H}$=7.4 Hz, 1.70-1.80 m (CH$_2$, 2H); 1.79 s (BH, 1H), 2.18 m (2CH$_2$, 4H); 2.98 s (CH$_3$, 3H); 3.26 m, (CH$_2$, 2H); 3.44 m (2CH$_2$, 4H).

$^{11}$B-NMR (Solvent: Acetonitrile-D$_3$): δ, ppm=−40.1 s, $^1J_{B,H}$=98 Hz.

Viscosity: 26.6 mPa·s (20° C.).

Decomposition temperature: above 280° C. (DSC/TGA; onset).

Example 7

N,N,N-tri-n-butyl-N-methylammonium hydrido-tricyano-borate—[n-Bu$_3$NCH$_3$][BH(CN)$_3$]

K[BH(CN)$_3$] + [(n-C$_4$H$_9$)$_3$NCH$_3$]Cl $\xrightarrow{H_2O}$ [(n-C$_4$H$_9$)$_3$NCH$_3$][BH(CN)$_3$] + KCl 8.84 g (68.5 mmol) K[BH(CN)$_3$] dissolved in 50 cm$^3$ water and 16.2 g (68.7 mmol) N,N,N-tri-n-butyl-N-methylammonium chloride, [n-Bu$_3$NCH$_3$]Cl in 50 cm$^3$ water are mixed together at room temperature. The product, N,N,N-tri-n-butyl-N-methylammonium tricyanohydridoborate is extracted with dichloromethane (100+50+50 cm$^3$ of CH$_2$Cl$_2$). The organic phase is washed two times with water (50+50 cm$^3$) and dried with Na$_2$SO$_4$. The solvent is distilled off and the residue is dried in vacuum at ca. 45° C. for 1 day. The yield of liquid at room temperature N,N,N-tri-n-butyl-N-methylammonium tricyanohydridoborate, [n-Bu$_3$NCH$_3$][BH(CN)$_3$], is 16.4 g (82%).

Content of chloride impurities: 24 ppm (ion-chromatography).

Viscosity: 149 mPa·s (20° C.).

$^1$H{$^{11}$B}-NMR (Solvent: Aceton-D$_6$): δ, ppm=1.00 t (3CH$_3$, 9H), $^3J_{H,H}$=7.4 Hz; 1.43 m (3CH$_2$, 6H); 1.80 s (BH, 1H), 1.75-1.86 m (3CH$_2$, 6H); 3.15 s (CH$_3$, 3H), 3.40 m, (3CH$_2$, 6H).

$^{11}$B-NMR (Solvent: Aceton-D$_6$): δ, ppm=−40.0 d, $^1J_{B,H}$=97 Hz.

Example 8 tetra-n-butylphosphonium hydrido-tricyanoborate—[n-Bu$_4$P][BH(CN)$_3$]

K[BH(CN)$_3$] + [(n-C$_4$H$_9$)$_4$P]OH $\xrightarrow{H_2O}$ [(n-C$_4$H$_9$)$_4$P][BH(CN)$_3$] + KOH 1.93 g (15.0 mmol) K[BH(CN)$_3$] dissolved in 10 cm$^3$ of water are mixed at room temperature with 10.4 g (10.5 cm$^3$, 15.0 mmol) 40% aqueous solution tera-n-butylphosphonium hydroxyde, [n-Bu$_4$P]OH. The product, tera-n-butylphosphonium tricyanohydrido-borate is extracted with dichloromethane (100+50+50 cm$^3$ of CH$_2$Cl$_2$). The organic phase is washed two times with water (50+50 cm$^3$) and dried with Na$_2$SO$_4$. The solvent is distilled off and the residue is dried in vacuum at ca. 45° C. for 2 day. The yield of liquid at room temperature tera-n-butylphosphonium tricyanohydridoborate, [n-Bu$_4$P][BH(CN)$_3$], is 4.86 g (89%).

$^1$H{$^{11}$B}-NMR (Solvent: Aceton-D$_6$): δ, ppm=0.98 t (4CH$_3$, 12H), $^3J_{H,H}$=7.3 Hz; 1.53 m (4CH$_2$, 8H); 1.62-1.74 m (4CH$_2$, 8H); 1.80 s (BH, 1H), 2.36 m, (4CH$_2$, 8H).

$^{11}$B-NMR (Solvent: Aceton-D$_6$): δ, ppm=−40.0 d, $^1J_{B,H}$=97 Hz.

Example 9

1-butyl-3-methylpyridinium hydrido-tricyano-borate—[BMPy][BH(CN)$_3$]

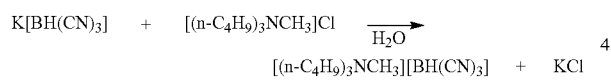 + K[BH(CN)$_3$] $\xrightarrow{H_2O}$

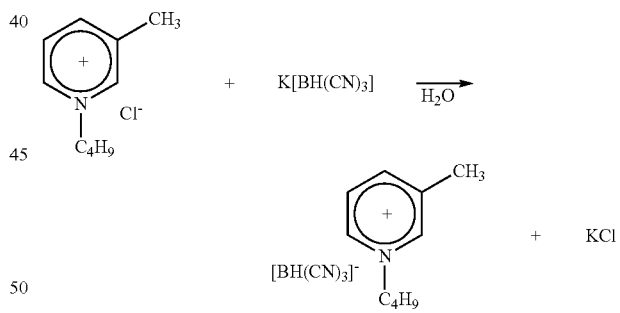 + KCl 8.08 g (62.7 mmol) K[BH(CN)$_3$] dissolved in 35 cm$^3$ of water and 11.63 g (62.6 mmol) of 1-butyl-3-methylpyridinium chloride, [BMPy]Cl, dissolved in 18 cm$^3$ of water are mixed together at room temperature. The product, 1-butyl-3-methylpyridinium tricyanohydridoborate is extracted with dichloromethane (100+50+50 cm$^3$ of CH$_2$Cl$_2$). The organic phase is washed two times with water (50+50 cm$^3$) and dried with Na$_2$SO$_4$. The solvent is distilled off and the residue is dried in vacuum at ca. 40° C. for one day. The yield of liquid at room temperature 1-butyl-3-methylpyridinium tricyanohydridoborate, [BMPy][BH(CN)$_3$], is 13.64 g (91%).

$^1$H-NMR (Solvent: Aceton-D$_6$): δ, ppm=0.99 t (CH$_3$, 3H), $^3J_{H,H}$=7.5 Hz; 1.45 m (CH$_2$, 2H); 1.74 d (1H, BH), $^1J_{H,B}$=97 Hz; 2.09 m (CH$_2$, 2H); 2.63 s (CH$_3$, 3H), 4.72 t (CH$_2$, 2H), $^3J_{H,H}$=7.6 Hz; 8.10 d,d (CH, 1H), $^3J_{H,H}$=7.0 Hz; 8.50 d (CH, 1H), $^3J_{H,H}$=8.0 Hz; 8.88 d (CH, 1H), $^3J_{H,H}$=6.1 Hz; 8.94 s (CH, 1H).

$^{11}$B-NMR (Solvent: Aceton-D$_6$): δ, ppm=−40.1 d, $^1J_{B,H}$=97 Hz.

Example 10 triethyl-sulfonium hydrido-tricyano-borate, [(C$_2$H$_5$)$_3$S]$^+$[BH(CN)$_3$]$^-$

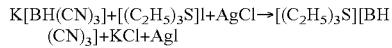

The solution of 52.34 g (308 mmol) AgNO$_3$ in 200 mL of water is treated with 27 mL 37% HCl. Precipitant (AgCl) is filtered off and washed 5 time with 200 mL of water. AgCl obtained in this way is vigorously stirred for 24 hours with 14.45 g (58.7 mmol) of triethyl sulfonium iodide, [Et$_3$S]I, in 50 mL of water. The yellow precipitant is filtered off and the aqueous solution of triethyl sulfonium chloride, [Et$_3$S]Cl, is reacted with 7.61 g (59.0 mmol) of potassium hydrido-tricyano-borate, K[BH(CN)$_3$]. The reaction mixture is extracted with 100+50+50 mL CH$_2$Cl$_2$. The organic phase is washed with 10+10+10 mL of water and dried with Na$_2$SO$_4$. The solution is filtered and the solvent is distilled off. The residue is dried in vacuum at 40-50° C. over night. 10.50 g (50.2 mmol) of liquid triethylsulfonium hydrido-tricyano-borate, [Et$_3$S][BH(CN)$_3$], is obtained Yield is 86% calculating on the triethyl sulfonium iodide used. The product is characterised with the NMR spectra.

[BH(CN)$_3$]$^-$
$^1$H-NMR (Solvent: CD$_3$CN), δ, ppm: 1.79 q, $^1J(^1H,^{11}B)$=98 Hz.
$^{11}$B-NMR (Solvent: CD$_3$CN), δ, ppm: −40.1d, $^1J(^1H,^{11}B)$=98 Hz, $^1J(^{13}C,^{11}B)$=66 Hz.
$^{13}$C-NMR (Solvent: CD$_3$CN), δ, ppm: 128.2 q,d, $^1J(^{13}C,^{11}B)$=66 Hz, $^1J(^1H,^{13}C)$=13 Hz,

[(C$_2$H$_5$)$_3$S]$^+$
$^1$H-NMR (Solvent: CD$_3$CN), δ, ppm: 1.43 t (CH$_3$), $^3J_{H,H}$=7.45 Hz, $^1J_{H,C}$=131 Hz; 3.23 q (CH$_2$), $^3J_{H,H}$=7.41 Hz, $^1J_{H,C}$=146 Hz.
$^{13}$C-NMR (Solvent: CD$_3$CN), δ, ppm: 9.0 q,m (CH$_3$), $^1J_{C,H}$=131 Hz, $^2J_{C,H}$=4 Hz; 33.3 μm (CH$_2$), $^1J_{C,H}$=146 Hz, $^{2,3}J_{C,H}$=2-4 Hz, $^1J_{C,C}$=34 Hz.

Viscosity and density of triethyl-sulfonium hydrido-tricyano-borate, [Et$_3$S][BH(CN)$_3$]:

| Temperature, ° C. | Viscosity, mPa · s | Density, g/cm$^3$ |
| --- | --- | --- |
| 20 | 14.65 | 0.981 |
| 40 | 8.45 | 0.967 |
| 60 | 5.50 | 0.954 |
| 80 | 3.87 | 0.941 |

Example 11 diphenyl-iodonium hydrido-tricyano-borate, [(C$_6$H$_5$)$_2$I]$^+$[BH(CN)$_3$]$^-$

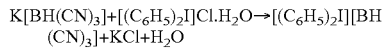

The solution 0.90 g (6.98 mmol) of K[BH(CN)$_3$] in 10 mL H$_2$O and the solution of 2.27 g (6.80 mmol) of diphenyl iodonium chloride monohydrate, [Ph$_2$I]Cl.H$_2$O in 150 mL CH$_2$Cl$_2$ are mixed together. The reaction mixture is diluted with 100 mL of water and two phase system is separated in the funnel. The aqueous phase is additionally extracted two times with 20 mL CH$_2$Cl$_2$. The combined organic phase is washed with 50 mL of water and dried with Na$_2$SO$_4$. The solution is filtered and the solvent is distilled off. The residue is dried in vacuum at 40-50° C. over night. 2.35 g (6.34 mmol) of diphenyl-iodonium hydrido-tricyano-borate, [(C$_6$H$_5$)$_2$I][BH(CN)$_3$], is obtained. Yield is 93% calculating on the diphenyl iodonium chloride monohydrate used. The product is characterised with the NMR spectra.

[BH(CN)$_3$]$^-$
$^1$H-NMR (Solvent: CD$_3$CN), δ, ppm: 1.90 q, $^1J(^1H,^{11}B)$=98 Hz.
$^{11}$B-NMR (Solvent: CD$_3$CN), δ, ppm: −39.9 d, $^1J(^1H,^{11}B)$=98 Hz.
$^{13}$C-NMR (Solvent: CD$_3$CN), δ, ppm: 128.2 q,d, $^1J(^{13}C,^{11}B)$=66 Hz, $^1J(^1H,^{13}C)$=13 Hz,

[(C$_6$H$_5$)$_2$I]$^+$
$^1$H-NMR (Solvent: CD$_3$CN), δ, ppm: 7.55 t (CH, 4H), $^3J_{H,H}$=7.5 Hz, 7.69 t (CH, 2H), $^3J_{H,H}$=7.5 Hz, 8.14 d,d (CH, 4H), $^3J_{H,H}$=8.5 Hz, $^4J_{H,H}$=0.8 Hz.
$^{13}$C-NMR (Solvent: CD$_3$CN), δ, ppm: 114.3 t,q (2C), J$_{C,H}$=11.9 Hz, J$_{C,H}$=2.1 Hz; 133.2 d,d (4C), $^1J_{C,H}$=167 Hz, J$_{C,H}$=8.1 Hz; 133.7 d,t (2C), $^1J_{C,H}$=165 Hz, J$_{C,H}$=7.4 Hz; 136.0 d,m (4C), $^1J_{C,H}$=169 Hz, J$_{C,H}$=7-8 Hz.

Example 12 ditolyl-iodonium hydrido-tricyano-borate, [(4-CH$_3$C$_6$H$_4$)$_2$I]$^+$[BH(CN)$_3$]$^-$

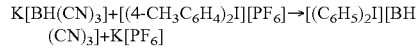

The solution 0.832 g (6.45 mmol) of K[BH(CN)$_3$] in 10 mL CH$_3$CN and the solution of 2.680 g (5.90 mmol) of ditolyl-iodonium hexafluorophosphate, [(4-CH$_3$C$_6$H$_4$)$_2$I][PF$_6$], in 5 mL CH$_3$CN are mixed together. The precipitate is filtered off and the solution is evaporated on rotary evaporator. The residue is dissolved in 20 mL CH$_2$Cl$_2$, the precipitant is filtered off and washed with 10 mL CH$_2$Cl$_2$. The solvent is evaporated on rotary evaporator and the residue is dried in vacuum at 40-50° C. over night. 2.226 g (5.58 mmol) of ditolyl-iodonium hydrido-tricyano-borate, [(4-CH$_3$C$_6$H$_4$)$_2$I][BH(CN)$_3$], is obtained Yield is 95% calculating on the ditolyl iodonium hexafluorophosphate used. The product is characterised with the NMR spectra.

[BH(CN)$_3$]$^-$
$^1$H-NMR (Solvent: CD$_3$CN), δ, ppm: 1.85 q, $^1J(^1H,^{11}B)$=99 Hz.
$^{11}$B-NMR (Solvent: CD$_3$CN), δ, ppm: −40.0 d, $^1J(^1H,^{11}B)$=99 Hz.
$^{13}$C-NMR (Solvent: CD$_3$CN), δ, ppm: 128.3 q,d, $^1J(^{13}C,^{11}B)$=66 Hz, $^1J(^1H,^{13}C)$=13 Hz.

[(4-CH$_3$C$_6$H$_4$)$_2$I]$^+$
$^1$H-NMR (Solvent: CD$_3$CN), δ, ppm: 2.38 s (CH$_3$, 3H); 7.36 d (CH, 4H), $^3J_{H,H}$=8.3 Hz; 7.99 d (CH, 4H), $^3J_{H,H}$=8.4 Hz.
$^{13}$C-NMR (Solvent: CD$_3$CN), δ, ppm: 21.4 q,t (2C, 2CH$_3$), $^1J_{C,H}$=128 Hz, $^3J_{C,H}$=4.2 Hz; 110.7 t (2C), J$_{C,H}$=12.0 Hz; 134.0 d,d,q (4C), $^1J_{C,H}$=164 Hz, J$_{C,H}$=5.8 Hz; 136.0 d,d (4C), $^1J_{C,H}$=170 Hz, J$_{C,H}$=5.7 Hz; 145.2 t,q (2C), J$_{C,H}$=6.5 Hz.

Example A

Formulations and Device

The following electrolyte formulations are synthesized to demonstrate the application of electrolyte formulations according to the invention relative to electrolyte formulations of the prior art containing emim TCB in dye sensitized solar cells.

The electrolyte formulations are prepared through mixing of one or more of 1,3-dimethylimidazolium iodide (mmimI), 1-propyl-3-methylimidazolium iodide (pmimI), iodine, N-butylbenzimidazole (NBB) and guanidinium thiocyanate (guaSCN) and the corresponding ionic liquid as indicated such as emim TCB and emim [BH(CN)$_3$] (emim MHB) or bmpl TCB and bmpl [BH(CN)$_3$] (N-butyl-N-methylpyrrolidinium monohydridotricyanoborate=bmpl MHB) in weight % as listed below.

| Electrolyte 1 | molar ratio [%] | theoretical value in weight % |
|---|---|---|
| I$_2$ | 3.1 | 3.5 |
| mmim I | 22.4 | 22.0 |
| pmim I | 22.4 | 24.8 |
| guaSCN | 1.2 | 0.6 |
| NBB | 6.2 | 4.8 |
| emim TCB | 44.7 | 44.3 |
| total | 100 | 100 |

Electrolyte 1 is measured three times.

| Electrolyte 2 | molar ratio [%] | theoretical value in weight % |
|---|---|---|
| I$_2$ | 3.1 | 3.6 |
| mmim I | 22.4 | 22.8 |
| pmim I | 22.4 | 25.7 |
| guaSCN | 1.2 | 0.7 |
| NBB | 6.2 | 4.9 |
| emim [BH(CN)$_3$] | 44.8 | 42.3 |
| total | 100 | 100 |

Electrolyte 2 is measured three times.

| Electrolyte 3 | weight % |
|---|---|
| I$_2$ | 1.3 |
| mmim I | 35 |
| guaSCN | 0.7 |
| NBB | 3 |
| emim TCB | 60 |
| total | 100 |

Electrolyte 3 is measured two times.

| Electrolyte 4 | weight % |
|---|---|
| I$_2$ | 1.3 |
| mmim I | 35 |
| guaSCN | 0.7 |
| NBB | 3 |
| emim [BH(CN)$_3$] | 60 |
| total | 100 |

Electrolyte 4 is measured two times.

| Electrolyte 5 | weight % |
|---|---|
| I$_2$ | 1.3 |
| mmim I | 35 |
| guaSCN | 0.7 |
| NBB | 3 |
| bmpl TCB | 60 |
| total | 100 |

Electrolyte 5 is measured two times.

| Electrolyte 6 | weight % |
|---|---|
| I$_2$ | 1.3 |
| mmim I | 35 |
| guaSCN | 0.7 |
| NBB | 3 |
| bmpl [BH(CN)$_3$] | 60 |
| total | 100 |

Electrolyte 6 is measured two times.

The above cited compounds are commercially available or are synthesized according to known literature methods.

The dye sensitized solar cells for the following measurements (masterplates) are commercially available from ISE (Institut für solare Energiesysteme, Freiburg), serial no. 010311 which are fabricated based on the disclosure of U.S. Pat. No. 5,728,487 or WO 2007/093961:

The used titaniumdioxide paste is commercially available from Dyesol, Australia, serial no. DSL 18 NRT and DSL 18NRT AO.

The titanium dioxide is screen printed three times: two times with the titaniumdioxide paste DSL 18 NRT (each layer thickness=2 μm and one time with the titaniumdioxide paste DSL 18NRT AO (layer thickness 5 to 6 μm).

The masterplate is irrigated with a solution of 30 mg Z907 dye in 62.5 ml ethanol for 6 hours.

The electrolyte formulations as described above are filled into the internal space of the prepared masterplate to produce the corresponding devices.

The dye Z907 is an amphiphilic ruthenium sensitizer Ru(2,2'-bipyridine 4,4'-dicarboxylic acid) (4,4'-dinonyl-2,2'-bipyridine)(NCS)$_2$ or synonymously [Ru(H2dcbpy)(dnbpy)(NCS)$_2$].

The measurements of photocurrent-voltage curves are carried out under Solarsimulator Sun 2000 from Abet Technologies, Model 11018, with temperature control for devices fabricated as described above containing electrolytes 1 to 6 placed on a black plate chilled down to 25° C. under 1 Sun illumination. The measured area of the solar cell is 5 mm to 25 mm.

Energy conversion efficiency is generally the ratio between the useful output of an energy conversion machine and the input of light radiation, in energy terms, determined by using adjustable resistant load to optimize the electric power output.

Table 1 summarizes the results of the measurements of the above cited electrolyte formulations as average values:

| Electrolyte | $J_{SC}$ [mAcm$^{-2}$] | $V_{OC}$ [V] | FF [%] | η [%] |
|---|---|---|---|---|
| 1* | 9.0 | 0.65 | 66.8 | 3.9 |
| 2 | 8.9 | 0.67 | 67.8 | 4.1 |
| 3* | 7.2 | 0.62 | 57.5 | 2.6 |
| 4 | 7.85 | 0.62 | 60.8 | 3.0 |

-continued

| Electrolyte | $J_{SC}$ [mAcm$^{-2}$] | $V_{OC}$ [V] | FF [%] | η [%] |
|---|---|---|---|---|
| 5* | 4.65 | 0.62 | 54.5 | 1.6 |
| 6 | 5.1 | 0.62 | 53.5 | 1.7 |

*not according to the invention $J_{SC}$ = short circuit current $V_{OC}$ = open circuit voltage FF = fill factor η = power conversion efficiency Table 1 documents that electrolytes comprising hydridotricyanoborate as anion perform better or equal than electrolytes comprising TCB as anion if the same cation is used.

Example B

Formulations and Device

The following electrolyte formulations are synthesized to demonstrate the unexpected advantage of electrolyte formulations according to the invention relative to electrolyte formulations of the prior art containing emim TCB.

The electrolyte formulations are prepared through mixing of one or more of 1,3-dimethylimidazolium iodide (mmimI), 1-ethyl-3-methylimidazolium iodide (emimI), 1-propyl-3-methylimidazolium iodide (pmimI), 1-allyl-3-methylimidazolium iodide (allylMIMI), iodine, N-butylbenzimidazole (NBB), guanidinium thiocyanate (guaSCN), γ-butyrolacton (GBL) and tetraethylenglycoldimethylether (TG) and the corresponding ionic liquid as indicated such as emim TCB, B3MPYR TCB (1-Butyl-3-methyl-pyridinium tetracyanoborate), emim [BH(CN)$_3$], bmpl [BH(CN)$_3$] (N-butyl-N-methylpyrrolidinium hydridotricyanoborate) or B3MPYR [BH(CN)$_3$] (1-Butyl-3-methyl-pyridinium hydridotricyanoborate) in weight % as listed below.

| Electrolyte 7 | weight % |
|---|---|
| I$_2$ | 3.5 |
| pmim I | 21 |
| mmim I | 20 |
| guaSCN | 0.5 |
| NBB | 5 |
| emim TCB | 25 |
| GBL | 25 |
| total | 100 |

| Electrolyte 8 | weight % |
|---|---|
| I$_2$ | 3.5 |
| pmim I | 21 |
| mmim I | 20 |
| guaSCN | 0.5 |
| NBB | 5 |
| emim MHB | 25 |
| GBL | 25 |
| total | 100 |

| Electrolyte 9 | weight % |
|---|---|
| I$_2$ | 3.5 |
| pmim I | 21 |
| mmim I | 20 |
| guaSCN | 0.5 |
| NBB | 5 |
| emim TCB | 25 |
| TG | 25 |
| total | 100 |

| Electrolyte 10 | weight % |
|---|---|
| I$_2$ | 3.5 |
| pmim I | 21 |
| mmim I | 20 |
| guaSCN | 0.5 |
| NBB | 5 |
| emim MHB | 25 |
| TG | 25 |
| total | 100 |

| Electrolyte 11 | weight % |
|---|---|
| I$_2$ | 4.1 |
| emim I | 27.9 |
| mmim I | 26.2 |
| guaSCN | 0.8 |
| NBB | 5.7 |
| emim TCB | 35.3 |
| total | 100 |

| Electrolyte 12 | weight % |
|---|---|
| I$_2$ | 4.3 |
| emim I | 29.0 |
| mmim I | 27.2 |
| guaSCN | 0.8 |
| NBB | 5.9 |
| emim MHB | 32.8 |
| total | 100 |

| Electrolyte 13 | weight % |
|---|---|
| I$_2$ | 4.3 |
| emim I | 15 |
| mmim I | 14.2 |
| allylMIMI | 15.1 |
| guaSCN | 0.8 |
| NBB | 5.9 |
| emim TCB | 44.7 |
| total | 100 |

| Electrolyte 14 | weight % |
|---|---|
| I$_2$ | 4.3 |
| emim I | 15 |
| mmim I | 14.2 |
| allylMIMI | 15.1 |
| guaSCN | 0.8 |

-continued

| Electrolyte 14 | weight % |
|---|---|
| NBB | 5.9 |
| emim MHB | 44.7 |
| total | 100 |

| Electrolyte 15 | weight % |
|---|---|
| $I_2$ | 3.5 |
| pmim I | 24.8 |
| mmim I | 22 |
| guaSCN | 0.6 |
| NBB | 4.8 |
| b3mpyr TCB | 44.6 |
| total | 100 |

| Electrolyte 16 | weight % |
|---|---|
| $I_2$ | 3.5 |
| pmim I | 24.8 |
| mmim I | 22 |
| guaSCN | 0.6 |
| NBB | 4.8 |
| b3mpyr MHB | 44.6 |
| total | 100 |

The above cited compounds are commercially available or are synthesized according to known literature methods.

The dye sensitized solar cells for the following measurements (masterplates) are commercially available from ISE (Institut für solare Energiesysteme, Freiburg), serial no. 010311 which are fabricated based on the disclosure of U.S. Pat. No. 5,728,487 or WO 2007/093961:

The used titaniumdioxide paste is commercially available from Dyesol, Australia, serial no. DSL 18 NRT and DSL 18NRT AO.

The titanium dioxide is screen printed three times: two times with the titaniumdioxide paste DSL 18 NRT (each layer thickness=2 μm) and one time with the titaniumdioxide paste DSL 18NRT AO (layer thickness 5 to 6 μm).

The masterplate is irrigated with a solution of 30 mg Z907 dye in 62.5 ml ethanol for 4 hours.

The electrolyte formulations as described above are filled into the internal space of the prepared masterplate to produce the corresponding devices.

The dye Z907 is an amphiphilic ruthenium sensitizer Ru(2,2'-bipyridine 4,4'-dicarboxylic acid) (4,4'-dinonyl-2,2'-bipyridine)(NCS)$_2$ or synonymously [Ru(H2dcbpy)(dnbpy)(NCS)$_2$].

The measurements of photocurrent-voltage curves are carried out under Solarsimulator Sun 2000 from Abet Technologies, Model 11018, with temperature control for devices fabricated as described above containing electrolytes 7 to 14 placed on a black plate chilled down to 25° C. under 1 Sun illumination. The measured area of the solar cell is 5 mm to 25 mm.

Energy conversion efficiency is generally the ratio between the useful output of an energy conversion machine and the input of light radiation, in energy terms, determined by using adjustable resistant load to optimize the electric power output.

Table 2 summarizes the results of the measurements of the above cited electrolyte formulations as average values:

| Electrolyte | $J_{SC}$ [mAcm$^{-2}$] | $V_{OC}$ [V] | FF [%] | η [%] |
|---|---|---|---|---|
| 7* | 9.9 | 0.62 | 67.3 | 4.2 |
| 8 | 9.8 | 0.63 | 0.68 | 4.2 |
| 9* | 8.3 | 0.62 | 0.61 | 3.1 |
| 10 | 8.5 | 0.63 | 0.59 | 3.2 |
| 11* | 8.3 | 0.62 | 0.67 | 3.5 |
| 12 | 8.7 | 0.62 | 0.66 | 3.6 |
| 13* | 7.5 | 0.61 | 0.66 | 3.0 |
| 14 | 7.3 | 0.61 | 0.67 | 3.0 |
| 15* | 7.8 | 0.58 | 0.45 | 2.0 |
| 16 | 8.1 | 0.58 | 0.44 | 2.1 |

*not according to the invention $J_{SC}$ = short circuit current $V_{OC}$ = open circuit voltage FF = fill factor η = power conversion efficiency Table 2 documents that electrolytes comprising hydridotricyanoborate as anion perform better or comparable to electrolytes comprising TCB as anion if the same cation is used.

Example C

Formulation and Device

The following electrolyte formulations are synthesized to demonstrate the unexpected advantage of electrolyte formulations according to the invention (emim MHB) relative to corresponding electrolyte formulations containing emim TCB.

The electrolyte formulations are prepared through mixing of 1,3-dimethylimidazolium iodide (mmimI), iodine, N-butylbenzimidazole (NBB), guanidinium thiocyanate (guaSCN) and the corresponding ionic liquid as indicated such as emim TCB, emim [BH(CN)$_3$] (emim MHB) or mixtures of emim TCB and emim MHB in weight % as listed below.

TABLE 3 electrolytes 11 to 15

| Ingredients in weight % | Electrolyte | | | | |
|---|---|---|---|---|---|
| | 17* | 18 | 19 | 20 | 21 |
| $I_2$ | 1.3 | 1.3 | 1.3 | 1.3 | 1.3 |
| mmimI | 35.0 | 35.0 | 35.0 | 35.0 | 35.0 |
| guaSCN | 0.7 | 0.7 | 0.7 | 0.7 | 0.7 |
| emim TCB | 60.0 | 45.0 | 30.0 | 15.0 | 0.0 |
| emim MHB | 0.0 | 15.0 | 30.0 | 45.0 | 60.0 |
| NBB | 3.0 | 3.0 | 3.0 | 3.0 | 3.0 |

*not according to the invention

The dye sensitized solar cells are fabricated as disclosed in U.S. Pat. No. 5,728,487 or WO 2007/093961:

A double-layer, mesoporous TiO$_2$ electrode was prepared as disclosed in Wang P et al., J. Phys. Chem. B 2003, 107, 14336, in particular page 14337, in order to obtain a photoanode consisting of a double layer structure. To prepare a transparent nanoporous TiO$_2$ electrode, a screen printing paste containing terpineol solvent and nanoparticulate TiO$_2$ of anatase phase with 20 nm diameter was deposited on a transparent conductive substrate to 5 mm×5 mm squared shape by using a hand printer. The paste was dried for 10 minutes at 120 degrees Celsius. Another screen printing paste containing $TiO_2$ with 400 nm diameter was then deposited on top of the nanoporous layer to prepare an opaque layer. The double layer film was then sintered at 500 degrees Celsius for an hour with the result of an underlying transparent layer (7 microns thick) and a top opaque layer (4 microns thick). After sintering, the electrode was immersed in 40 mM aqueous solution of $TiCl_4$ (Merck) for 30 minutes at 70 degrees Celsius and then rinsed with pure water sufficiently. Thus $TiCl_4$-treated electrode was dried at 500 degrees Celsius for 30 minutes just before dye sensitization. The electrode was dipped into a dye solution being 0.3 mM for the dye C106 and 0.075 mM for DINHOP (solvent mixture acetonitrile (Merck HPLC grade) and tert-butyl alcohol (Merck), v:v=1:1) for 64 hours at 6 degrees Celsius. The counter electrode was prepared with thermal pyrolysis method as disclosed in the reference above. A droplet of 5 mM solution of platonic acid (Merck) was casted at 8 ml/cm$^2$ and dried on a conductive substrate. The dye sensitized solar cell was assembled by using 30 micron thick Bynel (DuPont, USA) hot-melt film to seal up by heating. The internal space was filled with each of the electrolyte formulations as described above to produce the corresponding devices.

In order to obtain accurate light intensity level, Air Mass 1.5 Global (AM 1.5G) simulated sunlight is calibrated spectrally according to Seigo Ito et al, "Calibration of solar simulator for evaluation of dye-sensitized solar cells", Solar Energy Materials & Solar Cells, 82, 2004, 421.

The measurements of photocurrent-voltage curves are carried out under Air Mass 1.5 simulated sunlight (AM 1.5) with temperature control for devices fabricated as described above containing electrolytes 1 to 4 placed on a black plate chilled down to 25° C. under 1 Sun illumination. A photomask of 4 mm×4 mm is placed on top of the devices to define the light projection area. The cell gap is around 20 micron.

Energy conversion efficiency is generally the ratio between the useful output of an energy conversion machine and the input of light radiation, in energy terms, determined by using adjustable resistant load to optimize the electric power output.

Table 4-A summarizes the results of the measurements of the above cited electrolyte formulations:

| Electrolyte | $J_{SC}$ [mAcm$^{-2}$] | $V_{OC}$ [V] | FF | η [%] |
|---|---|---|---|---|
| 17* | 11.03 | 0.72 | 0.73 | 5.72 |
| 18 | 10.00 | 0.74 | 0.68 | 5.03 |
| 19 | 11.41 | 0.74 | 0.73 | 6.14 |
| 20 | 11.35 | 0.74 | 0.74 | 6.25 |
| 21 | 12.14 | 0.73 | 0.76 | 6.82 |

*not according to the invention $J_{SC}$ = short circuit current $V_{OC}$ = open circuit voltage FF = fill factor η = power conversion efficiency Table 4-A documents that electrolytes comprising monohydridotricyanoborate as anion or electrolytes comprising mixtures of monohydridotricyanoborate and tetracyanoborate anions perform better than electrolytes comprising TCB as anion if the same cation is used.

The performance of a heat stress test (85° C.) for electrolytes of table 4 documents that the electrolytes 18, 19 and 20 have the high efficiency of the inventive monohydridotricyanoborate and the high stability of tetracyanoborate.

The dye sensitized solar cells are fabricated and measured as disclosed before but with the dye Z907 without the additive DINHOP.

Table 4-B summarizes the results of the measurements of the above cited electrolyte formulations:

| Electrolyte | $J_{SC}$ [mAcm$^{-2}$] | $V_{OC}$ [V] | FF | η [%] |
|---|---|---|---|---|
| 17* | 10.63 | 0.71 | 0.64 | 4.84 |
| 18 | 11.66 | 0.72 | 0.66 | 5.55 |
| 19 | 11.96 | 0.71 | 0.68 | 5.79 |
| 20 | 12.41 | 0.71 | 0.68 | 6.03 |
| 21 | 11.63 | 0.73 | 0.70 | 5.88 |

*not according to the invention $J_{SC}$ = short circuit current $V_{OC}$ = open circuit voltage FF = fill factor η = power conversion efficiency Example D Formulation and Device The following electrolyte formulations are synthesized to demonstrate the unexpected advantage of electrolyte formulations according to the invention (emim MHB) together with a list of additives.

The electrolyte formulations are prepared through mixing of 1,3-dimethylimidazolium iodide (mmimI), iodine, guanidinium thiocyanate (guaSCN), emim [BH(CN)$_3$] (emim MHB) with and without additives as listed below.

guaI means guanidinium iodide.

TABLE 5

| | electrolytes 22 to 26 | | | | |
|---|---|---|---|---|---|
| Ingredients | Electrolyte | | | | |
| in weight % | 22 | 23 | 24 | 25 | 26 |
| I$_2$ | 1.5 | 1.5 | 1.5 | 1.4 | 1.5 |
| mmimI | 36.7 | 35.8 | 36.0 | 34.8 | 35.9 |
| guaSCN | 0.7 | 0.7 | 0.7 | 0.7 | 0.7 |
| emim MHB | 61.1 | 59.7 | 59.9 | 58.0 | 59.9 |
| NBB | 0.0 | 0.0 | 0.0 | 2.0 | 0.0 |
| Benzimidazole | 0.0 | 2.3 | 0.0 | 0.0 | 0.0 |
| guaI | 0.0 | 0.0 | 2.0 | 3.0 | 0.0 |
| emim SCN | 0.0 | 0.0 | 0.0 | 0.0 | 2.0 |

The dye sensitized solar cells are fabricated and measured as disclosed in example C with Z907, with the dye C106/DINHOP and with the dye D358.

Table 6 summarizes the results of the measurements of the above cited electrolyte formulations:

| Electrolyte | $J_{SC}$ [mAcm$^{-2}$] | $V_{OC}$ [V] | FF | η [%] |
|---|---|---|---|---|
| Z907 | | | | |
| 22 | 12.05 | 0.72 | 0.72 | 6.30 |
| 23 | 11.04 | 0.76 | 0.72 | 6.00 |
| 24 | 11.80 | 0.75 | 0.70 | 6.20 |
| 25 | 10.63 | 0.80 | 0.74 | 6.62 |
| 26 | 11.83 | 0.76 | 0.73 | 6.60 |

-continued

| Electrolyte | $J_{SC}$ [mAcm$^{-2}$] | $V_{OC}$ [V] | FF | η [%] |
|---|---|---|---|---|
| C106 | | | | |
| 22 | 13.75 | 0.68 | 0.71 | 6.57 |
| 23 | 12.50 | 0.71 | 0.73 | 6.53 |
| D358 | | | | |
| 22 | 12.18 | 0.65 | 0.68 | 5.36 |
| 24 | 12.75 | 0.64 | 0.68 | 5.62 |
| 25 | 10.73 | 0.72 | 0.72 | 5.52 |
| 26 | 11.75 | 0.67 | 0.70 | 5.45 |

Example E

Formulation and Device

The following electrolyte formulations are synthesized to demonstrate the unexpected advantage of electrolyte formulations according to the invention:

The electrolyte formulations are prepared through mixing of 1-ethyl-3-methylimidazolium iodide (emimI) or 1,1-dimethylpyrrolidinium iodide (mmpII), iodine, N-butylbenzimidazole (NBB), guanidinium thiocyanate (guaSCN) and the corresponding ionic liquid as indicated such as bmpl TCB, bmpl MHB (bmpl=1-butyl-1-methylpyrrolidinium), triethylsulfonium monohydridotricyanoborate (et3S MHB), 3-methylpyridinium monohydridotricyanoborate (B3MPYR MHB) and or.

TABLE 7 electrolytes 27 to 32

| Ingredients in weight % | Electrolyte | | | | | |
|---|---|---|---|---|---|---|
| | 27* | 28 | 29* | 30 | 31 | 32 |
| I$_2$ | 1.3 | 1.3 | 1.3 | 1.3 | 1.3 | 1.3 |
| emimI | 35.0 | 35.0 | 0.0 | 0.0 | 35.0 | 35.0 |
| mmpII | 0.00 | 0.00 | 35.00 | 35.00 | 0.00 | 0.00 |
| guaSCN | 0.7 | 0.7 | 0.7 | 0.7 | 0.7 | 0.7 |
| bmpl TCB | 60.0 | 0.00 | 60.0 | 0.00 | 0.00 | 0.00 |
| bmpl MHB | 0.00 | 60.0 | 0.00 | 60.0 | 0.00 | 0.00 |
| et3S MHB | 0.00 | 0.00 | 0.00 | 0.00 | 60.0 | 0.00 |
| B3MPYR MHB | 0.00 | 0.00 | 0.00 | 0.00 | 0.00 | 60.0 |
| NBB | 3.0 | 3.0 | 3.0 | 3.0 | 3.0 | 3.0 |

*not according to the invention

The dye sensitized solar cells are fabricated and measured as disclosed in example C but with the dye Z907.

Table 8 summarizes the results of the measurements of the above cited electrolyte formulations:

| Electrolyte | $J_{SC}$ [mAcm$^{-2}$] | $V_{OC}$ [V] | FF | η [%] |
|---|---|---|---|---|
| 27* | 9.27 | 0.72 | 0.60 | 4.02 |
| 28 | 11.38 | 0.74 | 0.64 | 5.37 |
| 29* | 5.42 | 0.71 | 0.62 | 2.38 |
| 30 | 7.37 | 0.72 | 0.58 | 3.10 |
| 31 | 11.81 | 0.71 | 0.71 | 5.95 |
| 32 | 11.78 | 0.69 | 0.61 | 4.95 |

*not according to the invention

The invention claimed is:

1. Compounds of formula I $$[Kt^{z+}]_z[BH(CN)_3]^- \quad \quad I$$

in which [Kt]$^{z+}$ denotes an inorganic or organic cation and z is 1, 2, 3 or 4, where sodium hydrido-tricyano-borate, potassium hydrido-tricyano-borate, silver hydrido-tricyano-borate and PPN[HB(CN)$_3$] are excluded.

2. A compound according to claim 1, wherein [Kt]$^{z+}$ is an organic cation selected from the group comprising iodonium, tritylium, sulfonium, oxonium, ammonium, phosphonium, uronium, thiouronium, guanidinium cations or heterocyclic cations.

3. A compound according to claim 1, in which Kt$^{z+}$ denotes an inorganic cation selected from the group of H$^+$, NO$^+$, Li$^+$, Mg$^{2+}$, Cu$^+$, Cu$^{2+}$, Zn$^{2+}$, Ca$^{2+}$, Y$^{+3}$, Yb$^{+3}$, La$^{+3}$, Sc$^{+3}$, Ce$^{+3}$, Nd$^{+3}$, Tb$^{+3}$, Sm$^{+3}$ and complex (ligands containing) metal cations an organic cation, which is a tritylium cation, in which the phenyl groups are optionally substituted by straight-chain or branched alkyl groups having 1 to 20 C atoms, straight-chain or branched alkenyl having 2 to 20 C atoms and one or more double bonds or straight-chain or branched alkynyl having 2 to 20 C atoms and one or more triple bonds, an oxonium cation of formula (1) or a sulfonium cation of formula (2)

$$[(R^\circ)_3O]^+ \quad \quad (1)$$

$$[(R^\circ)_3S]^+ \quad \quad (2),$$

where

R$^\circ$ each independently of one another denotes a straight-chain or branched alkyl group having 1-8 C atoms, non-substituted phenyl or phenyl which is substituted by R$^{1*}$, OR', N(R')$_2$, CN or halogen and in case of sulfonium cations of formula (2) additionally denotes each independently (R''')$_2$N, R' is independently of each other H, non-fluorinated, partially fluorinated or perfluorinated straight-chain or branched C$_1$- to C$_{18}$-alkyl, saturated C$_3$- to C$_7$-cycloalkyl, non-substituted or substituted phenyl, R$^{1*}$ is independently of each other non-fluorinated, partially fluorinated or perfluorinated straight-chain or branched C$_1$- to C$_{18}$-alkyl, saturated C$_3$- to C$_7$-cycloalkyl, non-substituted or substituted phenyl and R''' is independently of each other straight-chain or branched C$_1$ to C$_6$ alkyl;

an ammonium cation of formula (3)

$$[NR_4]^+ \quad \quad (3),$$

where

R in each case, independently of one another, denotes

H, OR', N(R')$_2$, with the proviso that a maximum of one R in formula (3) is OR' or N(R')$_2$, straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which is optionally substituted by straight-chain or branched alkyl groups having 1-6 C atoms, where one or two R may be fully substituted by halogens, and one or more of R are optionally partially substituted by halogens, and/or by —OH, —OR', —CN, —N(R')$_2$, —C(O)OH, —C(O)OR', —C(O)R', —C(O)N(R')$_2$, —SO$_2$N(R')$_2$, —C(O)X, —SO$_2$OH, —SO$_2$X, —NO$_2$, —SR', —S(O)R', and/or —SO$_2$R' and where one or two non-adjacent carbon atoms in R which are not in the α-position are optionally replaced by atoms and/or atom groups selected from the group consisting of —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— and —P(O)R'— where R' each independently is H, non-fluorinated, partially fluorinated or perfluorinated straight-chain or branched C$_1$- to C$_{18}$-alkyl, saturated C$_3$- to C$_7$-cycloalkyl, non-substituted or substituted phenyl and X each independently is halogen;

a phosphonium cation of formula (4)

$$[P(R^2)_4]^+ \qquad (4),$$

where

R$^2$ in each case, independently of one another, denotes H, OR' or N(R')$_2$, straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which is optionally substituted by straight-chain or branched alkyl groups having 1-6 C atoms, where one or two R$^2$ are optionally fully substituted by halogens, and one or more of R$^2$ are optionally partially substituted by halogens, in particular and/or by —OH, —OR', —CN, —N(R')$_2$, —C(O)OH, —C(O)OR', —C(O)R', —C(O)N(R')$_2$, —SO$_2$N(R')$_2$, —C(O)X, —SO$_2$OH, —SO$_2$X, —NO$_2$, —SR', —S(O)R', —SO$_2$R' and where one or two non-adjacent carbon atoms in R$^2$ which are not in the α-position may be replaced by atoms and/or atom groups selected from the group consisting of —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'— where R' each independently is H, non-fluorinated, partially fluorinated or perfluorinated straight-chain or branched C$_1$- to C$_{18}$-alkyl, saturated C$_3$- to C$_7$-cycloalkyl, non-substituted or substituted phenyl and X each independently is halogen;

a uronium cation of formula (5)

$$[C(NR^3R^4)(OR^5)(NR^6R^7)]^+ \qquad (5),$$

where

R$^3$ to R$^7$ each, independently of one another, denote H, where H is excluded for R$^5$, straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which is optionally substituted by straight-chain or branched alkyl groups having 1-6 C atoms, where one or two of the substituents R$^3$ to R$^7$ are optionally fully substituted by halogens, and one or more of R$^3$ to R$^7$ are optionally partially substituted by halogens, and/or by —OH, —OR', —N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', and/or —NO$_2$ and where one or two non-adjacent carbon atoms in R$^3$ to R$^7$ which are not in the α-position are optionally replaced by atoms and/or atom groups selected from the group —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— and —P(O)R'— where R' each independently is H, non-fluorinated, partially fluorinated or perfluorinated straight-chain or branched C$_1$- to C$_{18}$-alkyl, saturated C$_3$- to C$_7$-cycloalkyl, non-substituted or substituted phenyl and X each independently is halogen;

a thiouronium cation of formula (6)

$$[C(NR^3R^4)(SR^5)(NR^6R^7)]^+ \qquad (6),$$

where

R$^3$ to R$^7$ each, independently of one another, denote H, where H is excluded for R$^5$, straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which is optionally substituted by straight-chain or branched alkyl groups having 1-6 C atoms, where one or two of R$^3$ to R$^7$ are optionally fully substituted by halogens, and one or more of the substituents R$^3$ to R$^7$ are optionally partially substituted by halogens, and/or by —OH, —OR', —N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', and/or —NO$_2$ and where one or two non-adjacent carbon atoms in R$^3$ to R$^7$ which are not in the α-position are optionally replaced by atoms and/or atom groups selected from the group —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— and —P(O)R'— where R' each independently is H, non-fluorinated, partially fluorinated or perfluorinated straight-chain or branched C$_1$- to C$_{18}$-alkyl, saturated C$_3$- to C$_7$-cycloalkyl, non-substituted or substituted phenyl and X each independently is halogen;

a guanidinium cation of formula (7)

$$[C(NR^8R^9)(NR^{10}R^{11})(NR^{12}R^{13})]^+ \qquad (7),$$

where

R$^8$ to R$^{13}$ each, independently of one another, denote H, —CN, N(R')$_2$, —OR', straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which is optionally substituted by straight-chain or branched alkyl groups having 1-6 C atoms, where one or two of the substituents R$^8$ to R$^{13}$ are optionally fully substituted by halogens, and one or more of the substituents R$^8$ to R$^{13}$ are optionally partially substituted by halogens, and/or by —OH, —OR', —N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', and/or —NO$_2$ and where one or two non-adjacent carbon atoms in R$^8$ to $R^{13}$ which are not in the α-position are optionally replaced by atoms and/or atom groups selected from the group —O—, —S—, —S(O)—, —SO₂—, —SO₂O—, —C(O)—, —C(O)O—, —N⁺(R')₂—, —P(O)R'O—, —C(O)NR'—, —SO₂NR'—, —OP(O)R'O—, —P(O)(N(R')₂)NR'—, —P(R')₂=N— and —P(O)R'—, where R' each independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl and X each independently is halogen;

a heterocyclic cation of formula (8)

[HetN]^{z+}  (8)

which

[HetN]^{z+} denotes a heterocyclic cation selected from the group consisting of

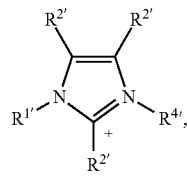
imidazolium

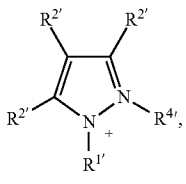
1 H-pyrazolium

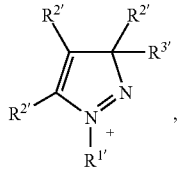
3 H-pyrazolium

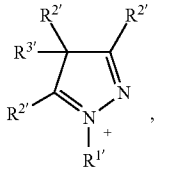
4 H-pyrazolium

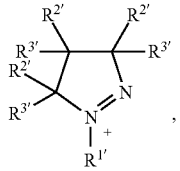
1-pyrazolinium

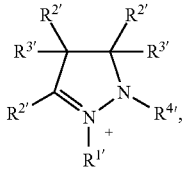
2-pyrazolinium

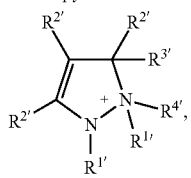
3-pyrazolinium

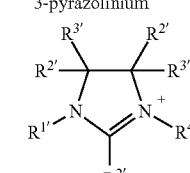
4,5-dihydroimidazolinium

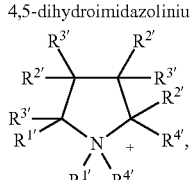
pyrrolidinium 2,3-dihydroimidazolinium 2,5-dihydroimidazolinium 1,2,4-triazolium

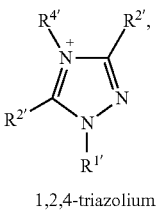
1,2,4-triazolium

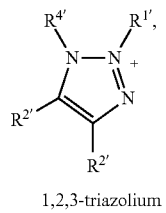
1,2,3-triazolium

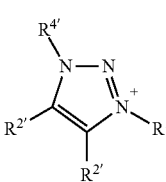
1,2,3-triazolium

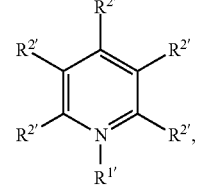
pyridinium

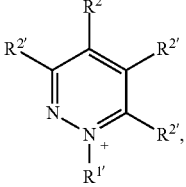
pyridazinium

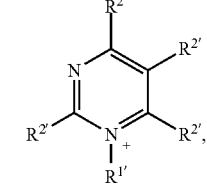
pyrimidinium

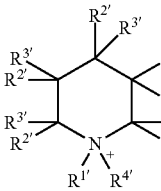
piperidinium

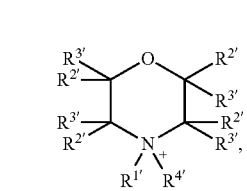
morpholinium

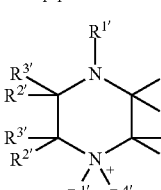
piperazinium

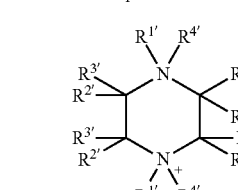
piperazinium

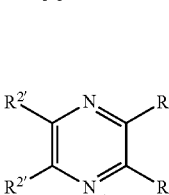
pyrazinium thiazolium oxazolium

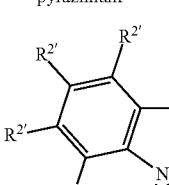
indolium

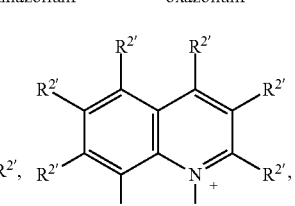
quinolinium

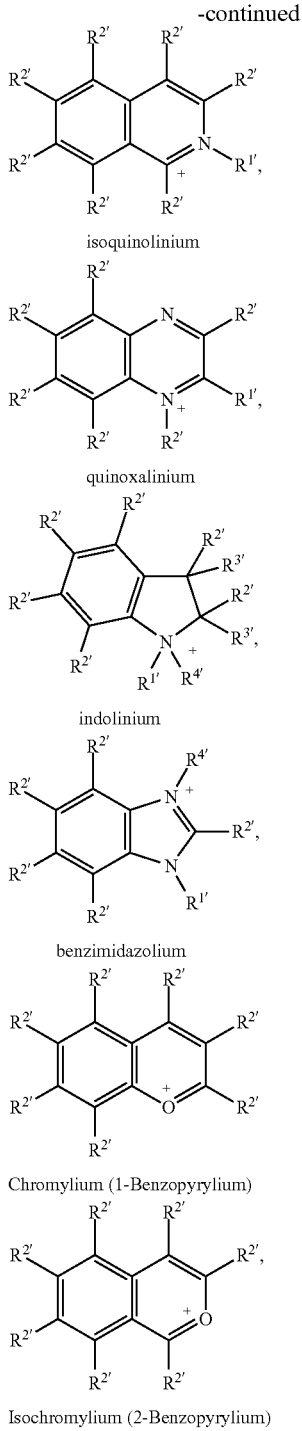

isoquinolinium quinoxalinium indolinium benzimidazolium

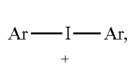

Pyrylium

Chromylium (1-Benzopyrylium)

Isochromylium (2-Benzopyrylium)

where
R$^{1'}$ to R$^{4'}$ each, independently of one another, denote
H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by straight-chain or branched alkyl groups having 1-6 C atoms,
saturated, partially or fully unsaturated heteroaryl, heteroaryl-C$_1$-C$_6$-alkyl or aryl-C$_1$-C$_6$-alkyl and
R$^{2'}$ denote additionally F, Cl, Br, I, —CN, —OR', —N(R')$_2$, —P(O)(R')$_2$, —P(O)(OR')$_2$, —P(O)(N(R')$_2$)$_2$, —C(O)R', —C(O)OR', —C(O)X, —C(O)N(R')$_2$, —SO$_2$N(R')$_2$, —SO$_2$OH, —SO$_2$X, —SR', —S(O)R', —SO$_2$R' and/or NO$_2$, with the proviso that R$^{1'}$, R$^{3'}$, R$^{4'}$ are in this case independently of each other H and/or a straight-chain or branched alkyl having 1-20 C atoms, and/or a straight-chain or branched alkenyl having 2-20 C atoms and one or more double bonds,
where the substituents R$^{1'}$, R$^{2'}$, R$^{3'}$ and/or R$^{4'}$ together optionally form a ring system,
where one to three substituents R$^{1'}$ to R$^{4'}$ are optionally fully substituted by halogens, and one or more of R$^{1'}$ to R$^{4'}$ are optionally partially substituted by halogens, and/or by —OH, —OR', N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', and/or —NO$_2$, but where R$^{1'}$ and R$^{4'}$ cannot simultaneously be fully substituted by halogens and where, in the substituents R$^{1'}$ to R$^{4'}$, one or two non-adjacent carbon atoms which are not bonded to the heteroatom are optionally replaced by atoms and/or atom groups selected from the —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'—,
where R' each independently is H, non-fluorinated, partially fluorinated or perfluorinated straight-chain or branched C$_1$- to C$_{18}$-alkyl, saturated C$_3$- to C$_7$-cycloalkyl, non-substituted or substituted phenyl and X each independently is halogen
or
a iodonium cation of formula (9)

$$Ar\!-\!\underset{+}{I}\!-\!Ar, \tag{9}$$

where
the aryl group Ar denotes each independently of each other aryl with 6 to 30 C atoms which is non-substituted or substituted with at least a straight-chain or branched alkyl group having 1 to 20 C atoms, a straight-chain or branched alkenyl group having 2 to 20 C atoms and one or more double bonds, a straight-chain or branched alkynyl group having 2 to 20 C atoms and one or more triple bonds, R$^{1*}$, NO$_2$, SR'', N(R')$_2$, CN and/or halogen,
where R' each independently is H, non-fluorinated, partially fluorinated or perfluorinated straight-chain or branched C$_1$- to C$_{18}$-alkyl, saturated C$_3$- to C$_7$-cycloalkyl, non-substituted or substituted phenyl,
where R$^{1*}$ each independently is non-fluorinated, partially fluorinated or Perfluorinated straight-chain or branched C$_1$- to C$_{18}$-alkyl, saturated C$_3$- to C$_7$-cycloalkyl, non-substituted or substituted phenyl, and
halogen is F, Cl, Br or I.

4. A process for preparing a compound of formula I according to claim 1 in which [Kt]$^{z+}$ is another cation than the alkali metal cation in the starting material and z denotes 1, 2, 3 or 4 in a salt-exchange reaction, comprising
reacting an alkali metal salt of formula I-1

[Me]$^+$[BH(CN)$_3$]$^-$     I-1 in which [Me]$^+$ is an alkali metal cation
or
reacting

H[BH(CN)$_3$]

with a compound of formula V

KtA     V, in which
Kt has a meaning of an organic cation or inorganic cation other than the alkali metal cation of the compound of formula I-1 or H$^+$ and
A denotes F$^-$, Cl$^-$, Br$^-$, I$^-$, OH$^-$, [HF$_2$]$^-$, [CN]$^-$, [SCN]$^-$, [R$_1$COO]$^-$, [R$_1$OC(O)O]$^-$, [R$_1$SO$_3$]$^-$, [R$_2$COO]$^-$, [R$_2$SO$_3$]$^-$, [R$_1$OSO$_3$]$^-$, [PF$_6$]$^-$, [BF$_4$]$^-$, [SO$_4$]$^{2-}$, [HSO$_4$]$^{1-}$, [NO$_3$]$^-$, [(R$_2$)$_2$P(O)O]$^-$, [R$_2$P(O)O$_2$]$^{2-}$, [(R$_1$O)$_2$P(O)O]$^-$, [(R$_1$O)P(O)O$_2$]$^{2-}$, [(R$_1$O)R$_1$P(O)O]$^-$, tosylate, malonate which is optionally substituted by straight-chain or branched alkyl groups having 1 to 4 C atoms, [HOCO$_2$]$^-$ or [CO$_3$]$^{2-}$, with the proviso that [SO$_4$]$^{2-}$ and [CO$_3$]$^{2-}$ are only for the synthesis of compounds of formula I having another metal cation than the alkali metal cation of the compound of formula I-1,
R$_1$ is each independently of another a straight-chain or branched alkyl group having 1 to 12 C atoms and
R$_2$ is each independently of one another a straight-chain or branched perfluorinated alkyl group having 1 to 12 C atoms.

5. An electrolyte formulation comprising at least one compound of formula I according to claim 1.

6. An electrochemical and/or optoelectronic device comprising an electrolyte formulation according to claim 5.

7. A method for cationic polymerization or photo polymerization or for photo acid generative, comprising initiating said cationic polymerization or photo polymerization, or generating said photo acid by a compound of formula I according to claim 3 in which [Kt]$^{z+}$ is a cation of formula (2), (5), (6), (9), tritylium, pyrylium, 1-benzopyrylium or 2-benzopyrylium which acts as a cationic polymerization initiator, photo-polymerization initiator or photo-acid generator.

8. A media for a chemical reaction, a catalyst and/or a media in a catalytical process, a conducting salt, a component of electrolytes for the application in electrochemical cells, a component of supporting electrolytes for an electrochemical process, a surfactant, a phase-transfer catalyst, a trainer, an extractant; an antistatic additive, a plasticiser; a heat-transfer-medium, a modifier for a membrane or textile material; a lubricant, an additive to a lubricant composition or to an engineering fluid; a hydraulic fluid or an additive to a hydraulic fluid, comprising a compound of formula I according to claim 1 in which [Kt]$^{z+}$ is an organic cation or H$^+$ and z is 1, 2, 3 or 4.

9. A compound according to claim 1, in which Kt$^{z+}$ denotes an inorganic cation selected from the group consisting of H$^+$, NO$^+$, Li$^+$, Mg$^{2+}$, Cu$^+$, Cu$^{2+}$, Zn$^{2+}$, Ca$^{2+}$, Y$^{+3}$, Yb$^{+3}$, La$^{+3}$, Sc$^{+3}$, Ce$^{+3}$, Nd$^{+3}$, Tb$^{+3}$, Sm$^{+3}$ and xomplex (ligands containing) metal cations, wherein the metal is selected from the group consisting of rare-earths, transitions metals and noble metals.

10. A compound according to claim 1, in which Kt$^{z+}$ denotes an inorganic cation selected from the group consisting of H$^+$, NO$^+$, Li$^+$, Mg$^{2+}$, Cu$^+$, Cu$^{2+}$, Zn$^{2+}$, Ca$^{2+}$, Y$^{+3}$, Yb$^{+3}$, La$^{+3}$, Sc$^{+3}$, Ce$^{+3}$, Nd$^{+3}$, Tb$^{+3}$, Sm$^{+3}$ and complex (ligands containing) metal cations, wherein the metal is selected from the group consisting of rhodium, ruthenium, iridium, palladium, platinum, osmium, cobalt, nickel, iron, chromium, molybdenum, tungsten, vanadium, titanium, zirconium, hafnium, thorium, uranium and gold.

11. A compound according to claim 3, in which Kt$^{z+}$ denotes
a heterocyclic cation of formula (8)

[HetN]$^{z+}$     (8)

which
[HetN]$^{z+}$ denotes a heterocyclic cation selected from the group consisting of

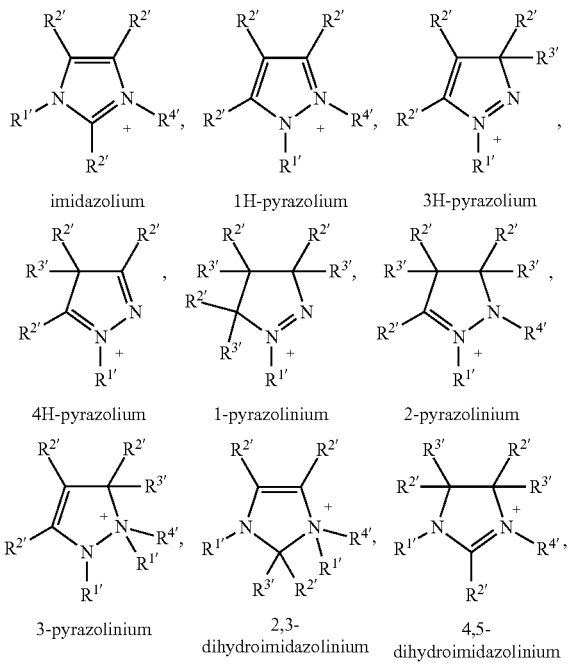

imidazolium, 1H-pyrazolium, 3H-pyrazolium, 4H-pyrazolium, 1-pyrazolinium, 2-pyrazolinium, 3-pyrazolinium, 2,3-dihydroimidazolinium, 4,5-dihydroimidazolinium

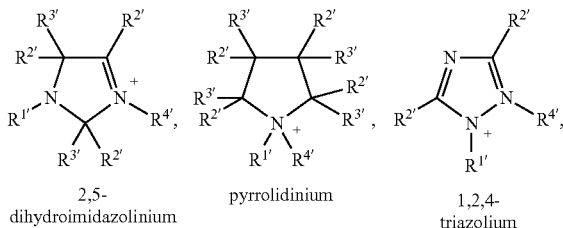

2,5-dihydroimidazolinium, pyrrolidinium, 1,2,4-triazolium

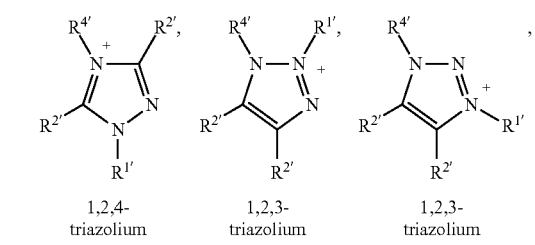

1,2,4-triazolium, 1,2,3-triazolium, 1,2,3-triazolium

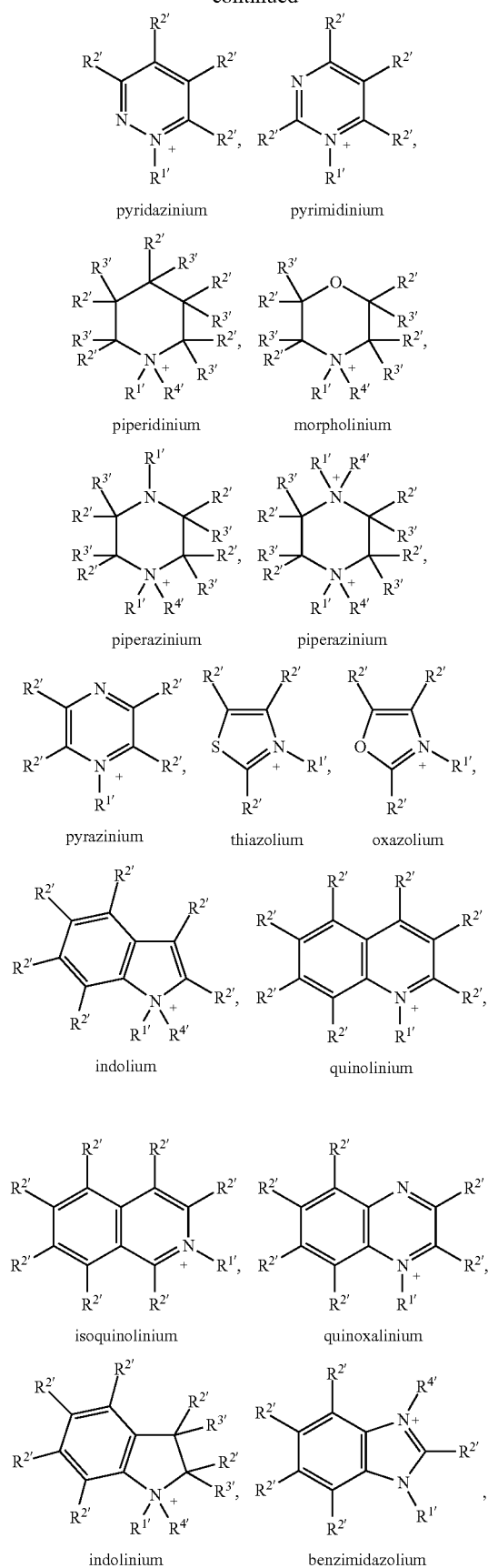
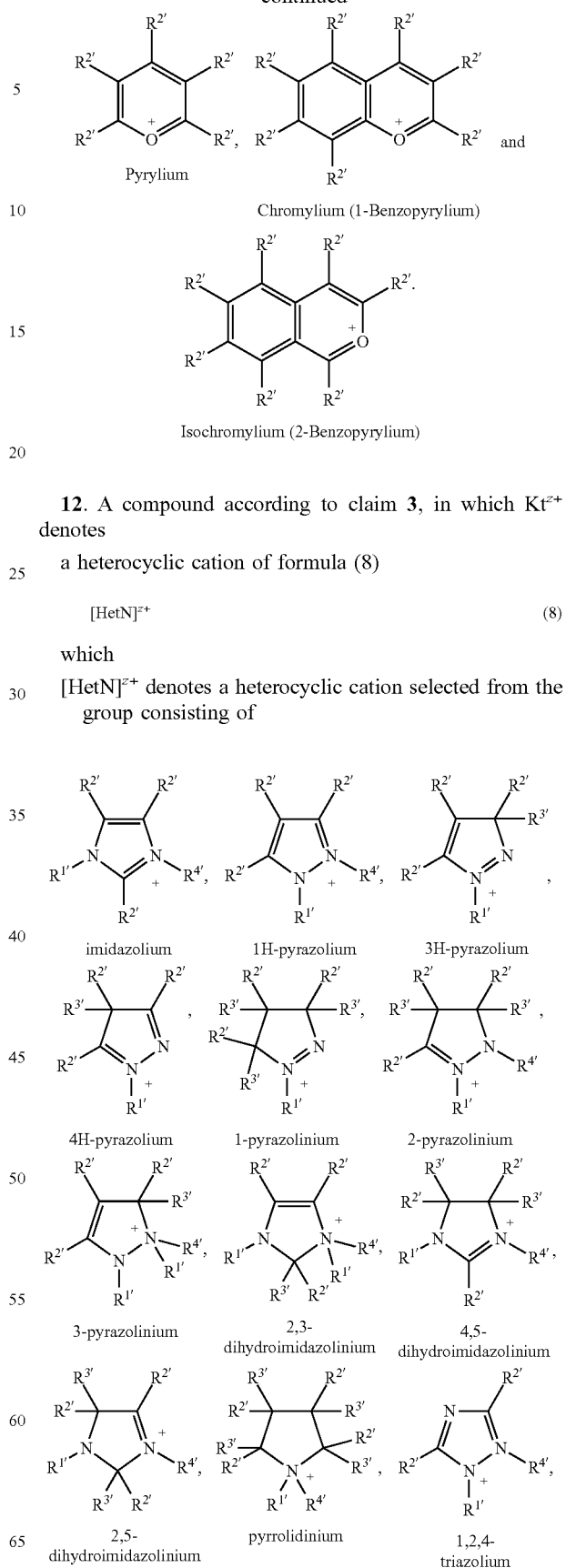
12. A compound according to claim 3, in which $Kt^{z+}$ denotes
a heterocyclic cation of formula (8)
$$[HetN]^{z+} \qquad (8)$$
which
$[HetN]^{z+}$ denotes a heterocyclic cation selected from the group consisting of

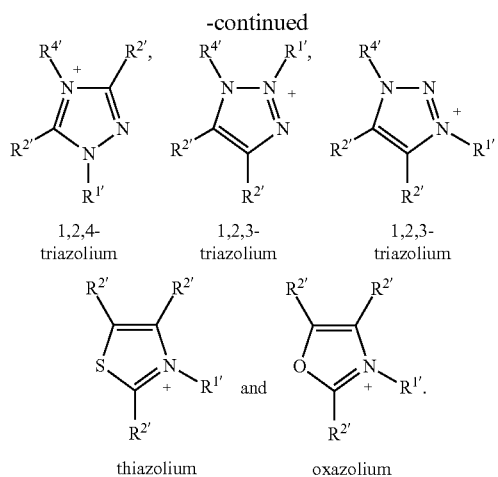

1,2,4-triazolium    1,2,3-triazolium    1,2,3-triazolium thiazolium    oxazolium 13. A compound according to claim 3, in which $Kt^{z+}$ denotes a heterocyclic cation of formula (8)

[HetN]$^{z+}$          (8)

which

[HetN]$^{z+}$ denotes a heterocyclic cation selected from the group consisting of

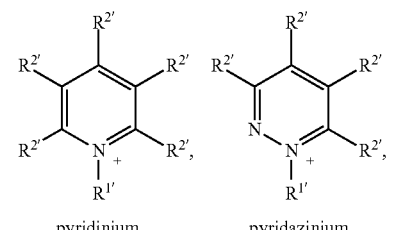

pyridinium    pyridazinium

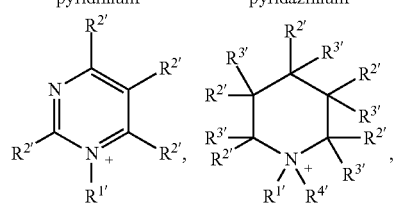

pyrimidinium    piperidinium

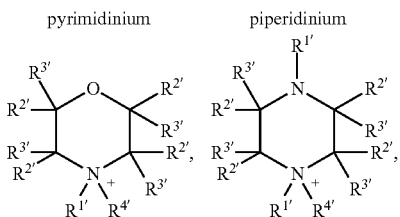

morpholinium    piperazinium

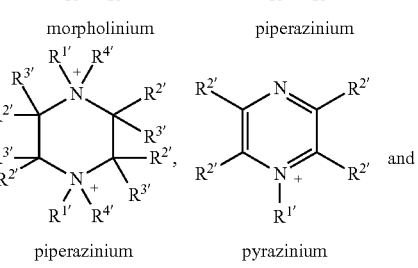

piperazinium    pyrazinium

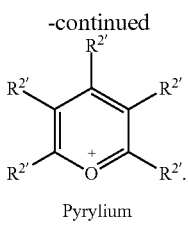

Pyrylium

14. A compound according to claim 3, in which $Kt^{z+}$ denotes a heterocyclic cation of formula (8)

[HetN]$^{z+}$          (8)

which

[HetN]$^{z+}$ denotes a heterocyclic cation selected from the group consisting of

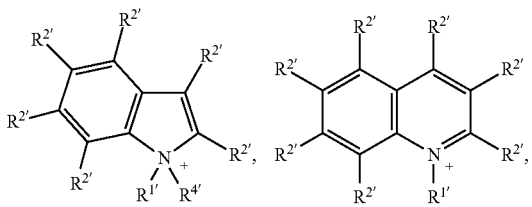

indolium    quinolinium

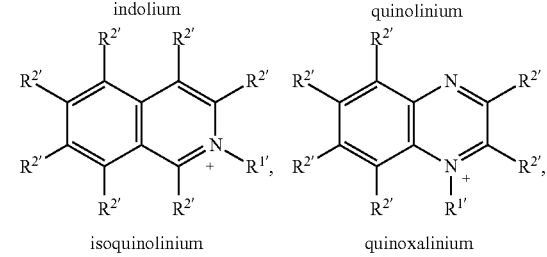

isoquinolinium    quinoxalinium

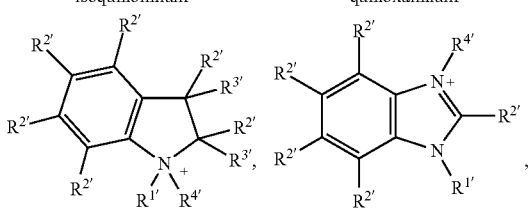

indolinium    benzimidazolium

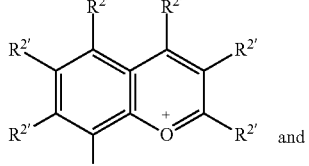

Chromylium (1-Benzopyrylium)

Isochromylium (2-Benzopyrylium)

* * * * *